(12) United States Patent
Berg et al.

(10) Patent No.: US 7,595,319 B2
(45) Date of Patent: Sep. 29, 2009

(54) COMPOUNDS HAVING SELECTIVE INHIBITING EFFECT AT GSK3

(75) Inventors: Stefan Berg, Sodertalje (SE); Sven Hellberg, Sodertalje (SE); Peter Soderman, Sodertalje (SE)

(73) Assignee: AstraZeneca AB, Sodertalje (SE)

( * ) Notice: Subject to any disclaimer, the term of this patent is extended or adjusted under 35 U.S.C. 154(b) by 480 days.

(21) Appl. No.: 10/539,546

(22) PCT Filed: Dec. 15, 2003

(86) PCT No.: PCT/SE03/01956

§ 371 (c)(1),
(2), (4) Date: Jun. 16, 2005

(87) PCT Pub. No.: WO2004/055006

PCT Pub. Date: Jul. 1, 2004

(65) Prior Publication Data

US 2006/0173014 A1    Aug. 3, 2006

(30) Foreign Application Priority Data

Dec. 17, 2002  (SE)  .................................... 0203752

(51) Int. Cl.
*A61K 31/497* (2006.01)
*A61K 31/50* (2006.01)
*A61K 31/501* (2006.01)
*C07D 241/02* (2006.01)
*C07D 401/00* (2006.01)
*C07D 403/00* (2006.01)
*C07D 405/00* (2006.01)
*C07D 409/00* (2006.01)
*C07D 411/00* (2006.01)
*C07D 413/00* (2006.01)
*C07D 417/00* (2006.01)
*C07D 419/00* (2006.01)

(52) U.S. Cl. ............................ 514/252.11; 514/255.06; 544/357; 544/405

(58) Field of Classification Search .................. None
See application file for complete search history.

(56) References Cited

U.S. PATENT DOCUMENTS

| 2004/0186113 | A1* | 9/2004 | Berg et al. ............. 514/255.05 |
| 2006/0052396 | A1* | 3/2006 | Berg et al. ............. 514/255.06 |
| 2006/0116362 | A1* | 6/2006 | Berg et al. ............... 514/210.2 |
| 2006/0116385 | A1 | 6/2006 | Berg et al. |

FOREIGN PATENT DOCUMENTS

| WO | WO 0168612 A2 | 9/2001 |
| WO | WO 03004472 A1 | 1/2003 |

OTHER PUBLICATIONS

Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
International Search Report dated Apr. 20, 2004 for International Application No. PCT/SE2003/001956.
International-Type Search Report dated Sep. 10, 2003 for International Application No. PCT/SE2003/001956.
Office Action dated Sep. 22, 2008 for U.S. Appl. No. 10/539,545.
Office Action dated Sep. 4, 2008 for U.S. Appl. No. 10/539,543.

* cited by examiner

*Primary Examiner*—James O Wilson
*Assistant Examiner*—Jeffrey H Murray
(74) *Attorney, Agent, or Firm*—Kenneth F. Mitchell

(57) ABSTRACT

Selective phenyl substituted aminopyrazine inhibitors of GSK3 useful for the prevention and/or treatment of cognitive disorders.

3 Claims, No Drawings

COMPOUNDS HAVING SELECTIVE INHIBITING EFFECT AT GSK3

FIELD OF THE INVENTION

The present invention relates to new compounds of formula I, as a free base or a pharmaceutically acceptable salt, solvate or solvate of salt thereof, to pharmaceutical formulations containing said compounds and to the use of said compounds in therapy. The present invention further relates to a process for the preparation of compounds of formula I and to new intermediates used therein.

BACKGROUND OF THE INVENTION

Glycogen synthase kinase 3 (GSK3) is a serine/threonine protein kinase composed of two isoforms (α and β), which are encoded by distinct genes but are highly homologous within the catalytic domain. GSK3 is highly expressed in the central and peripheral nervous system. GSK3 phosphorylates several substrates including tau, β-catenin, glycogen synthase, pyruvate dehydrogenase and elongation initiation factor 2b (eIF2b). Insulin and growth factors activate protein kinase B, which phosphorylates GSK3 on serine 9 residue and inactivates it.

Alzheimer's Disease (AD) Dementias, and Taupathies.

AD is characterized by cognitive decline, cholinergic dysfunction and neuronal death, neurofibrillary tangles and senile plaques consisting of amyloid-β deposits. The sequence of these events in AD is unclear, but is believed to be related. Glycogen synthase kinase 3β (GSK3β) or Tau (τ) phosphorylating kinase selectively phosphorylates the microtubule associated protein τ in neurons at sites that are hyperphosphorylated in AD brains. Hyperphosphorylated protein τ has lower affinity for microtubules and accumulates as paired helical filaments, which are the main components that constitute neurofibrillary tangles and neuropil threads in AD brains. This results in depolymerization of microtubules, which leads to dying back of axons and neuritic dystrophy. Neurofibrillary tangles are consistently found in diseases such as AD, amyotrophic lateral sclerosis, parkinsonism-dementia of Gaum, corticobasal degeneration, dementia pugilistica and head trauma, Down's syndrome, postencephalatic parkinsonism, progressive supranuclear palsy, Niemann-Pick's Disease and Pick's Disease. Addition of amyloid-β to primary hippocampal cultures results in hyperphosphorylation of τ and a paired helical filaments-like state via induction of GSK3β activity, followed by disruption of axonal transport and neuronal death (Imahori and Uchida., J. Biochem 121: 179-188, 1997). GSK3β preferentially labels neurofibrillary tangles and has been shown to be active in pre-tangle neurons in AD brains. GSK3 protein levels are also increased by 50% in brain tissue from AD patients. Furthermore, GSK3β phosphorylates pyruvate dehydrogenase, a key enzyme in the glycolytic pathway and prevents the conversion of pyruvate to acetyl-Co-A (Hoshi et al., PNAS 93:2719-2723, 1996). Acetyl-Co-A is critical for the synthesis of acetylcholine, a neurotransmitter with cognitive functions. Thus, GSK3β inhibition may have beneficial effects in progression as well as the cognitive deficits associated with Alzheimer's disease and other above-referred to diseases.

Chronic and Acute Neurodegenerative Diseases.

Growth factor mediated activation of the PI3K/Akt pathway has been shown to play a key role in neuronal survival. The activation of this pathway results in GSK3β inhibition. Recent studies (Bhat et. al., PNAS 97:11074-11079 (2000)) indicate that GSK3β activity is increased in cellular and animal models of neurodegeneration such as cerebral ischemia or after growth factor deprivation. For example, the active site phosphorylation was increased in neurons vulnerable to apoptosis, a type of cell death commonly thought to occur in chronic and acute degenerative diseases such as Alzheimer's Disease, Parkinson's Disease, amyotrophic lateral sclerosis, Huntington's Disease and HIV dementia, ischemic stroke and head trauma. Lithium was neuroprotective in inhibiting apoptosis in cells and in the brain at doses that resulted in the inhibition of GSK3β. Thus GSK3β inhibitors could be useful in attenuating the course of neurodegenerative diseases.

Bipolar Disorders (BD)

Bipolar Disorders are characterised by manic episodes and depressive episodes. Lithium has been used to treat BD based on its mood stabilising effects. The disadvantage of lithium is the narrow therapeutic window and the danger of overdosing that can lead to lithium intoxication. The recent discovery that lithium inhibits GSK3 at therapeutic concentrations has raised the possibility that this enzyme represents a key target of lithium's action in the brain (Stambolic et al., Curr. Biol. 6:1664-1668, 1996; Klein and Melton; PNAS 93:8455-8459, 1996). Inhibition of GSK3β may therefore be of therapeutic relevance in the treatment of BD as well as in AD patients that have affective disorders.

Schizophrenia

GSK3 is involved in signal transduction cascades of multiple cellular processes, particularly during neural development. Kozlovsky et al (Am J Psychiatry May 2000; 157(5): 831-3) found that GSK3β levels were 41% lower in the schizophrenic patients than in comparison subjects. This study indicates that schizophrenia involves neurodevelopmental pathology and that abnormal GSK3 regulation could play a role in schizophrenia. Furthermore, reduced β-catenin levels have been reported in patients exhibiting schizophrenia (Cotter et al., Neuroreport 9:1379-1383 (1998)).

Diabetes

Insulin stimulates glycogen synthesis in skeletal muscles via the dephosphorylation and thus activation of glycogen synthase. Under resting conditions, GSK3 phosphorylates and inactivates glycogen synthase via dephosphorylation. GSK3 is also over-expressed in muscles from Type II diabetic patients (Nikoulina et al., Diabetes February 2000; 49(2): 263-71). Inhibition of GSK3 increases the activity of glycogen synthase thereby decreasing glucose levels by its conversion to glycogen. GSK3 inhibition may therefore be of therapeutic relevance in the treatment of Type I and Type II diabetes, diabetic neuropathy and diabetes related disorders.

Hair Loss

GSK3 phosphorylates and degrades β-catenin. β-catenin is an effector of the pathway for keratonin synthesis. β-catenin stabilisation may be lead to increase hair development. Mice expressing a stabilised β-catenin by mutation of sites phosphorylated by GSK3 undergo a process resembling de novo hair morphogenesis (Gat et al., Cell Nov. 25, 1998; 95 (5):

605-14)). The new follicles formed sebaceous glands and dermal papilla, normally established only in embryogenesis. Thus GSK3 inhibition may offer treatment for baldness.

Oral Contraceptives

Vijajaraghavan et al. (Biol Reprod June 2000; 62 (6):1647-54) reported that GSK3 is high in motile versus immotile sperm. Immunocytochemistry revealed that GSK3 is present in the flagellum and the anterior portion of the sperm head. These data suggest that GSK3 could be a key element underlying motility initiation in the epididymis and regulation of mature sperm function. Inhibitors of GSK3 could be useful as contraceptives for males.

DISCLOSURE OF THE INVENTION

The object of the present invention is to provide compounds having a selective inhibiting effect at GSK3 as well as having a good bioavailability. The compounds fall within the generic formula I:

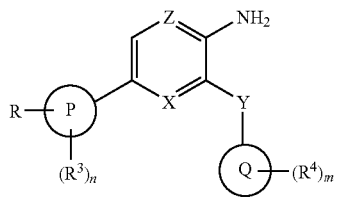

wherein:

Z is N;

Y is $CONR^5$;

X is N;

P is phenyl;

Q is phenyl or a 5 or 6 membered heteroaromatic ring containing one or more heteroatoms independently selected from N, O or S;

R is selected from $C_{0-6}alkyl(SO_2)NR^1R^2$, $C_{0-6}alkylCONR^1R^2$ and $OC_{1-6}alkylNR^1R^2$;

$R^1$ and $R^2$ are independently selected from hydrogen, $C_{1-6}alkyl$, $C_{1-6}alkylNR^6R^7$, $C_{1-6}alkylOR^6$ and a 5 or 6 membered heterocyclic ring containing one or more heteroatoms independently selected from N, O, or S and wherein said $C_{1-6}alkyl$ or heterocyclic ring may be optionally substituted by A;

$R^1$ and $R^2$ may together form a substituted 5 or 6 membered heterocyclic ring containing one or more heteroatoms independently selected from N, O, or S and said heterocyclic ring may be optionally substituted by A;

$R^3$ and $R^4$ is independently selected from halo, nitro, trifluoromethyl, $C_{0-6}alkylCN$, $C_{0-6}alkylOR^6$, $C_{0-6}alkylCONR^6R^7$, $C_{0-6}alkylNR^6(CO)R^7$, $C_{0-6}alkylCOR^6$, $C_{0-6}alkyl(SO_2)NR^6R^7$;

m is 0 or 1;

n is 0 or 1;

$R^5$ is hydrogen;

$R^6$ and $R^7$ are independently selected from hydrogen and $C_{1-6}alkyl$;

$R^6$ and $R^7$ may together form a substituted 5 or 6 membered heterocyclic ring containing one or more heteroatoms independently selected from N, O, or S one or more heteroatoms independently selected from N, O or S and said heterocyclic ring may be optionally substituted by A;

A is $C_{1-6}alkyl$;

as a free base or a pharmaceutically acceptable salt, solvate or solvate of a salt thereof.

In one aspect of the invention the following compounds are provided:

3-Amino-N-(3-nitrophenyl)-6-[4-(pyrrolidin-1-ylsulfonyl)phenyl]pyrazine-2-carboxamide;

3-Amino-6-[4-(pyrrolidin-1-ylsulfonyl)phenyl]-N-1H-tetrazol-5-ylpyrazine-2-carboxamide;

N-[3-(Acetylamino)phenyl]-3-amino-6-[4-[(4-methyl-1-piperazinyl)sulfonyl]phenyl]-2-pyrazinecarboxamide;

3-Amino-N-[3-(aminosulfonyl)phenyl]-6-[4-[(4-methyl-1-piperazinyl)sulfonyl]phenyl]-2-pyrazinecarboxamide;

as a free base or a pharmaceutically acceptable salt, solvate or solvate of a salt thereof;

3-Amino-6-[4-({[(1R)-2-methoxy-1-methylethyl]amino}sulfonyl)phenyl]-N-pyridin-3-ylpyrazine-2-carboxamide hydrochloride;

3-Amino-6-[4-({[(1S)-2-methoxy-1-methylethyl]amino}sulfonyl)phenyl]-N-pyridin-3-ylpyrazine-2-carboxamide hydrochloride;

3-Amino-N-(2-methoxyphenyl)-6-{4-[(4-methylpiperazin-1-yl)sulfonyl]phenyl}pyrazine-2-carboxamide hydrochloride;

3-Amino-6-(4-{[(2-ethoxyethyl)amino]sulfonyl}phenyl)-N-pyridin-3-ylpyrazine-2-carboxamide hydrochloride;

3-Amino-N-(4-methoxyphenyl)-6-{4-[(4-methylpiperazin-1-yl)sulfonyl]phenyl}pyrazine-2-carboxamide hydrochloride;

3-Amino-N-[2-(aminocarbonyl)phenyl]-6-{4-[(4-methylpiperazin-1-yl)sulfonyl]phenyl}pyrazine-2-carboxamide hydrochloride;

3-Amino-N-[3-(aminocarbonyl)phenyl]-6-{4-[(4-methylpiperazin-1-yl)sulfonyl]phenyl}pyrazine-2-carboxamide hydrochloride;

3-Amino-N-(3-cyanophenyl)-6-{4-[(4-methylpiperazin-1-yl)sulfonyl]phenyl}pyrazine-2-carboxamide hydrochloride;

3-Amino-N-(2-bromophenyl)-6-{4-[(4-methylpiperazin-1-yl)sulfonyl]phenyl}pyrazine-2-carboxamide hydrochloride;

3-Amino-N-(3-bromophenyl)-6-{4-[(4-methylpiperazin-1-yl)sulfonyl]phenyl}pyrazine-2-carboxamide hydrochloride;

3-Amino-6-{4-[(4-methylpiperazin-1-yl)sulfonyl]phenyl}-N-1H-pyrazol-3-ylpyrazine-2-carboxamide hydrochloride;

3-Amino-N-[4-(aminocarbonyl)-1H-pyrazol-3-yl]-6-{4-[(4-methylpiperazin-1-yl)sulfonyl]phenyl}pyrazine-2-carboxamide hydrochloride;

3-Amino-N-1H-imidazol-2-yl-6-{4-[(4-methylpiperazin-1-yl)sulfonyl]phenyl}pyrazine-2-carboxamide hydrochloride;

3-amino-6-[3-fluoro-4-[2-(4-morpholinyl)ethoxy]phenyl]-N-3-pyridinyl-2-pyrazinecarboxamide hydrochloride;

3-Amino-6-[4-[[(1-ethyl-3-piperidinyl)amino]sulfonyl]phenyl]-N-3-pyridinyl-2-pyrazinecarboxamide hydrochloride;

3-Amino-6-[4-[[bis(2-methoxyethyl)amino]sulfonyl]phenyl]-N-3-pyridinyl-2-pyrazinecarboxamide hydrochloride;
3-Amino-6-[4-[[(3-methylbutyl)amino]sulfonyl]phenyl]-N-3-pyridinyl-2-pyrazinecarboxamide hydrochloride;
3-Amino-6-[4-[[[(1S)-2-methoxy-1-methylethyl]amino]carbonyl]phenyl]-N-3-pyridinyl-2-pyrazinecarboxamide hydrochloride;
3-Amino-N-3-pyridinyl-6-[4-[[[2-(1-pyrrolidinyl)ethyl]amino]carbonyl]phenyl]-2-pyrazinecarboxamide hydrochloride;
3-Amino-N-(3-methoxyphenyl)-6-[4-[(4-methyl-1-piperazinyl)sulfonyl]phenyl]-2-pyrazinecarboxamide hydrochloride;
N-(3-Acetylphenyl)-3-amino-6-[4-[(4-methyl-1-piperazinyl)sulfonyl]phenyl]-2-pyrazinecarboxamide hydrochloride;
3-Amino-6-[4-[(4-methyl-1-piperazinyl)sulfonyl]phenyl]-N-[3-(trifluoromethyl)phenyl]-2-pyrazinecarboxamide hydrochloride;

or as a free base or an alternative a pharmaceutically acceptable salt, solvate or solvate of a salt thereof;

Another aspect of the invention the compounds of formula XIX, which are useful as intermediates in the preparation of compounds of formula I, are provided

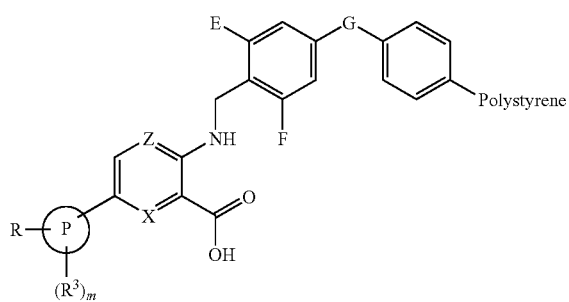

wherein R, $R^3$, P, X, Z, and m are as defined above, and wherein E and F are a methoxy group or hydrogen and G is a spacer chain containing atoms selected from oxygen and carbon; as a free base or a salt, solvate or solvate of a salt thereof.

In yet another aspect of the invention the following compounds, which are useful as intermediates in the preparation of compounds of formula I, are provided:
3-Amino-6-bromo-N-pyridin-3-ylpyrazine-2-carboxamide;
1-[(4-Bromophenyl)sulfonyl]pyrrolidine;
4-(Pyrrolidin-1-ylsulfonyl)phenylboronic acid;
4-Bromo-N-[(1R)-2-hydroxy-1-methylethyl]benzenesulfonamide;
4-Bromo-N-[(1R)-2-methoxy-1-methylethyl]benzenesulfonamide;
4-Bromo-N-[(1S)-2-methoxy-1-methylethyl]benzenesulfonamide;
Methyl 3-amino-6-[4-(pyrrolidin-1-ylsulfonyl)phenyl]pyrazine-2-carboxylate;
4-[(4-Methylpiperazin-1-yl)sulfonyl]phenylboronic acid;
Methyl 3-amino-6-[4-[(4-methyl-1-piperazinyl)sulfonyl]phenyl]pyrazine-2-carboxylate;
3-Amino-6-[4-[(4-methyl-1-piperazinyl)sulfonyl]phenyl]-2-pyrazinecarboxylic acid;
4-[2-(4-Bromo-2-fluorophenoxy)ethyl]morpholine;
4-Bromo-N-(1-ethyl-3-piperidinyl)benzenesulfonamide;
4-Bromo-N,N-bis(2-methoxyethyl)benzenesulfonamide;
4-Bromo-N-(3-methylbutyl)-benzenesulfonamide;
4-Bromo-N-(2-ethoxyethyl)benzenesulfonamide;
Methyl 3-{[2,6-dimethoxy-4-(2-phenylethoxy)benzyl]amino}-6-[4-(pyrrolidin-1-ylsulfonyl)phenyl]pyrazine-2-carboxylate polystyrene;
3-{[2,6-Dimethoxy-4-(2-phenylethoxy)benzyl]amino}-6-[4-(pyrrolidin-1-ylsulfonyl)phenyl]pyrazine-2-carboxylic acid polystyrene;
4-{5-Amino-6-[(pyridin-3-ylamino)carbonyl]pyrazin-2-yl}benzoic acid;

as a free base or a salt, solvate or solvate of a salt thereof.

Listed below are definitions of various terms used in the specification and claims to describe the present invention.

For the avoidance of doubt it is to be understood that where in this specification a group is qualified by 'hereinbefore defined', 'defined hereinbefore', 'is as defined above' or 'are as defined above' the said group encompasses the first occurring and broadest definition as well as each and all of the preferred definitions for that group.

For the avoidance of doubt it is to be understood that in this specification '$C_{0-6}$' means a carbon group having 0, 1, 2, 3, 4, 5 or 6 carbon atoms.

In this specification, unless stated otherwise, the term "alkyl" includes both straight and branched chain alkyl groups. $C_{1-6}$alkyl may be methyl, ethyl, n-propyl, i-propyl, n-butyl, i-butyl, s-butyl, t-butyl, n-pentyl, i-pentyl, t-pentyl, neo-pentyl, hexyl.

The term "alkoxy" as used herein, unless stated otherwise includes "alkyl" O groups in which "alkyl" is as hereinbefore defined. $C_{1-5}$alkoxy may be methoxy, ethoxy, n-propoxy, i-propoxy, n-butoxy, i-butoxy, s-butoxy, t-butoxy, n-pentyloxy, i-pentyloxy, t-pentyloxy, neo-pentyloxy.

In this specification, unless stated otherwise, the term "5 or 6 membered heteroaromatic ring containing one or more heteroatoms independently selected from N, O, or S" may be, but are not limited to, furyl, isoxazolyl, isothiazolyl, oxazolyl, pyrazinyl, pyrazolyl, pyridazinyl, pyridyl, pyrimidyl, pyrrolyl, thiazolyl, thienyl or imidazolyl.

In this specification, unless stated otherwise, the term "5 or 6 membered heterocyclic ring containing one or more heteroatoms independently selected from N, O, or S" may be, but are not limited to, imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl or thiomorpholinyl.

In this specification, unless stated otherwise, the term halogen may be fluorine, chlorine, bromine or iodine. The term Hal in the formulas means halogen.

The present invention relates to the use of compounds of formula I as hereinbefore defined as a free base as well as to the salts, solvates and solvates of salts thereof. Salts for use in pharmaceutical compositions will be pharmaceutically acceptable salts, but other salts may be useful in the production of the compounds of formula I.

Both organic and inorganic acids can be employed to form non-toxic pharmaceutically acceptable acid addition salts of the compounds, e.g. hydrochlorides of this invention. In addition, a suitable pharmaceutically acceptable salt of the compounds of the invention, which is sufficiently acidic is an alkali metal salt, an alkaline earth metal salt or a salt with an organic base, which affords a physiologically-acceptable cation.

It will be understood that certain compounds of the present invention may exist in solvated, for example hydrated, as well as unsolvated forms. It is to be understood that the present invention encompasses all such solvated forms which possess the above-mentioned activity.

Some compounds of formula I may have chiral centres and/or geometric isomeric centres E- and Z-isomers), and it is to be understood that the invention encompasses all such diastereoisomers, optical and geometric isomers that possess GSK3 inhibitory activity.

It is to be understood that the present invention relates to any and all tautomeric forms of the compounds of formula I.

An object of the invention is to provide compounds of formula I for therapeutic use, especially compounds that are useful for the prevention and/or treatment of conditions associated with glycogen synthase kinase-3 (GSK3) in mammals including man. Particularly, compounds of formula I exhibiting a selective affinity for GSK-3.

It is also an object of the invention to provide compounds with a therapeutic effect after oral administration.

Methods of Preparation

Another aspect of the present invention provides a process for preparing a compound of formula I as a free base or a pharmaceutically acceptable salt, solvate or solvate of a salt thereof.

Throughout the following description of such processes it is understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis" T. W. Green, P. G. M. Wuts, Wiley-Interscience, New York, 1999.

Methods of Preparation of Intermediates

The process for the preparation of the intermediates, wherein Y, X, Z, P, Q, R, $R^1$, $R^2$, $R^3$, $R^4$, $R^5$, $R^6$, $R^7$, A, m and n are, unless specified otherwise, defined as in formula I, comprises of:

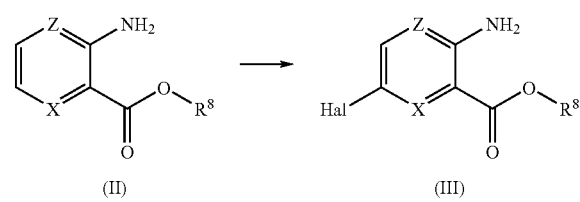

(i) halogenation of a compound of formula II, wherein X and Z are N, $R^8$ is hydrogen, $C_{1-6}$alkyl or when $R^8$ is hydrogen in the form of the acid or a salt such as a sodium salt, to obtain a compound of formula III, where Hal is halogen, may be carried out using a suitable halogenating reagent e.g. iodine, bromine, chlorine, halide salts for example ICl, BrCl or HOCl or other suitable halogenation reagents e.g. N-bromosuccinimide or phosphorous tribromide. The reaction may be catalysed by metals or acids such as Fe, Cu-salts, acetic acid or sulfuric acid or aided by oxidising agents e.g. nitric acid, hydrogen peroxide or sulfur trioxide. The reaction may be carried out in a suitable solvent such as water, acetic acid or chloroform at a temperature in the range of $-70°$ C. to $+100°$ C.

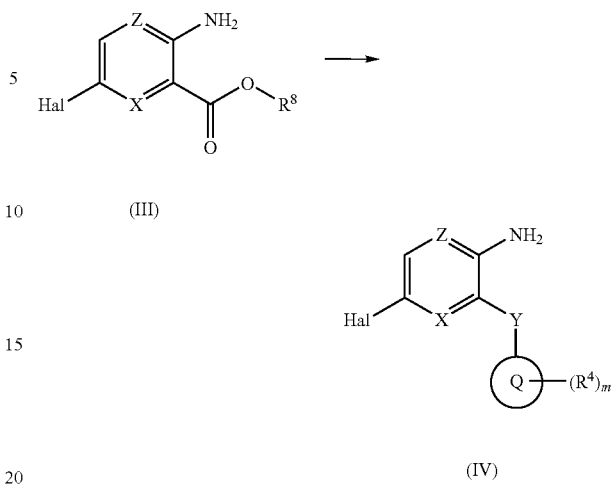

(ii) amidation of a compound of formula III, wherein X and Z are N, $R^8$ is $C_{1-6}$alkyl to obtain a compound of formula IV, wherein Y is $CONR^5$ and $R^4$, Q and m are as defined above may be carried out by treating a compound of formula III with the appropriate amine such as a compound of formula V, wherein Q is phenyl or a 5 or 6 membered heteroaromatic ring containing one or more heteroatoms selected from N, O or S, $R^4$ and m are as defined above. The reaction may be performed neat or using a suitable solvent such as N,N-dimethylformamide, methylene chloride or ethyl acetate at a temperature ranging from $-25°$ C. to $+150°$ C. The reaction may be aided by using a base such as potassium carbonate, trietylamine or 1,8-diazabicyclo[5.4.0]undec-7-ene, or an acid such as trimethylaluminum or p-toulenesulfonic acid.

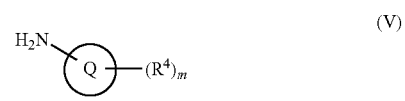

(iii) amidation of a compound of formula III, wherein $R^8$ is hydrogen, to obtain a compound of formula IV, wherein Y is $CONR^5$, m are as defined above, and $R^4$ is a substituent that is not susceptible to certain coupling agents, may be performed by activation of a compound of formula III by treating the compound with coupling reagents such as 1,3-diisopropyl-carbodiimide, 1-[3-(dimethylamino)propyl]-3-ethylcarbodiimide hydrochloride, 1,3-dicyclohexylcarbodiimide, O-(benzotriazol-1-yl)-N,N,N',N'-tetramethyluronium tetrafluoroborate, O-(benzotriazol-1-yl)-N,N,N',N'-tetramethyluronium hexafluorophosphate, 1,1'-carbonyldiimidazole or O-(7-azabenzotriazol-1-yl)-N,N,N',N'-tetramethyluronium hexafluorophosphate where the reaction may be aided by the addition of 1-hydroxybenzotriazole hydrate, or using an acyl halide reagent such as cyanuric chloride, oxalyl chloride, thionyl chloride or bromotrispyrrolidinophosphonium hexafluorophosphate, followed by treatment with the appropriate amine such as a compound of formula V in a suitable solvent such as methylene chloride chloroform, acetonitrile or tetrahydrofuran at a reaction temperature between $0°$ C. and reflux. The reaction may be aided by using a base such as potassium carbonate or a trialkylamine e.g triethylamine or N-ethyl-N,N-diisopropylamine.

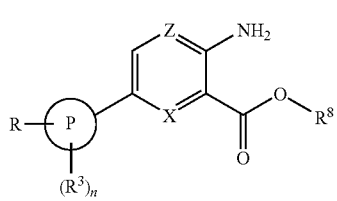

(VI)

(iv) conversion of a compound of formula III to a compound of formula VI, wherein X and Z are N, $R^8$ is $C_{1-6}$alkyl and R, $R^3$, P and n are as defined above, may be carried out by a de-halogen coupling with a suitable compound of formula XVIa-c.

The reaction may be carried out by coupling of a compound of formula III with an appropriate aryl boronic acid or a boronic ester of formula XVIa-c (the boronic acid or boronic ester may be formed in situ using the compounds of formula XI, XIII, XV or XXI and conditions described in (xii)). The reaction may be carried out using a suitable palladium catalyst such as $Pd(PPh_3)_4$, $Pd(dppf)Cl_2$ or $Pd(OAc)_2$ with or without a suitable ligand such as P(tert-butyl)$_3$ or 2-(dicyclohexylphosphino)biphenyl in the presence of a suitable base such as an alkylamine e.g. triethylamine, or potassium carbonate, potassium phosphate, sodium carbonate, sodium hydroxide or cesium fluoride, or a nickel catalyst such as nickel on charcoal or Ni(dppe)Cl$_2$ together with Zn and sodium triphenylphosphine trimetasulfonate. A suitable base such as an alkylamine e.g. is triethylamine, or potassium carbonate, potassium phosphate, sodium carbonate, sodium hydroxide or cesium fluoride may be used in the reaction, which reactions are performed in a temperature range between +20° C. and +160° C. using an oil bath or a microwave oven in a suitable solvent such as ethanol, water, toluene, tetrahydrofuran, glycol dimethyl ether or N,N-dimethylformamide or mixtures thereof.

(v) conversion of a compound of formula VI, wherein $R^8$ is $C_{1-6}$alkyl, to a compound of formula VI, wherein $R^8$ is hydrogen, may be carried out in a suitable solvent such as tetrahydrofuran or water or mixtures thereof in the presence of a suitable base such as potassium carbonate, sodium hydroxide or lithium hydroxide at a reaction temperature between +20° C. and +60° C.

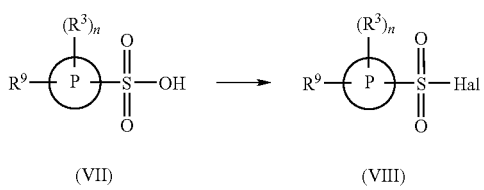

(VII)          (VIII)

(vi) halogenating a compound of formula VII, wherein $R^9$ is halogen e.g. bromine, or $NH_2$ and P, $R^3$ and n are as defined above, to obtain a compound of formula VIII may be carried out by treatment of a compound of formula VII with a halogenation reagents such as thionyl chloride or oxalyl chloride. The reaction may be performed neat or in a suitable solvent such as tetrahydrofuran, dioxane or methylene chloride at a temperature range between −20° C. and +60° C.;

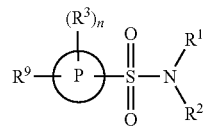

(IX)

(vii) amidation of a compound of formula VIII, wherein $R^9$ is halogen e. g. bromine, or $NH_2$, and P, $R^3$ and n are as defined above, to obtain a compound of formula IX, may be carried out by reacting a compound of formula VIII with the suitable amine $HNR^1R^2$. The reaction may be performed in a suitable solvent such as tetrahydrofuran, dioxane, N,N-dimethylformamide or methylene chloride with or without a suitable base such as a trialkylamine e.g. triethylamine, or potassium carbonate, sodium hydroxide or sodium hydrogen carbonate in a temperature range between 0° C. and +50° C.

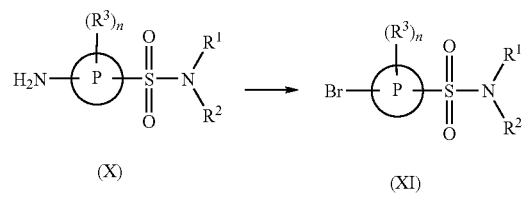

(X)          (XI)

(viii) conversion of a compound of formula X to obtain a compound of formula XI, wherein $R^1$, $R^2$, $R^3$, n and P are as defined above, may be carried out by treatment of a compound of formula X with sodium nitrite and hydrobromic acid followed by the addition of a bromide source such as CuBr in an appropriate solvent such as water at a temperature range between 0° C. and +5° C.

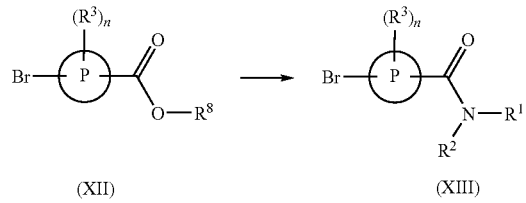

(XII)          (XIII)

(ix) formation of an amide of formula XIII, wherein $R^1$, $R^2$, $R^3$, n and P are as defined above, may be carried out by treating a compound of formula XII, wherein $R^8$ is $C_{1-6}$alkyl, with the appropriate amine $HNR^1R^2$. The reaction can be performed neat or using a suitable solvent such as N,N-dimethylformamide, methylene chloride or ethyl acetate at a temperature ranging from −25° C. to +150° C. The reaction may be aided by using a base such as potassium carbonate, trietylamine or 1,8-diazabicyclo[5.4.0]undec-7-ene or an acid such as trimethylaluminum or p-toulenesulfonic acid.

(x) amidation of a compound of formula XII, wherein $R^8$ is hydrogen and $R^3$, n and P are as defined above to obtain a compound of formula XIII may be performed by activation of a compound of formula XII by treating the compound with coupling reagents such as 1,3-diisopropylcarbodiimide, 1-[3-(dimethylamino)propyl]-3-ethylcarbodiimide hydrochloride, 1,3-dicyclohexylcarbodiimide, O-(benzotriazol-1-yl)-N,N,N',N'-tetramethyluronium tetrafluoroborate, O-(benzotriazol-1-yl)-N,N,N',N'-tetramethyluronium hexafluorophosphate, 1,1'-carbonyldiimidazole or O-(7-aza-benzotriazol-1-yl)-N,N,N',N'-tetramethyluronium hexafluorophosphate where the reaction may be aided by the addition of 1-hydroxybenzotriazole hydrate, or using an acyl halide reagent such as cyanuric chloride, oxalyl chloride, thionyl chloride or bromotrispyrrolidinophosphonium hexafluorophosphate, followed by treatment with the appropriate amine HNR$^1$R$^2$. The reaction may be carried out in a suitable solvent such as N,N-dimethylformamide, acetonitrile or methylene chloride at a temperature ranging from $-25°$ C. to $+150°$ C., with or without a suitable base such as an alkylamine e.g. triethylamine, N-ethyl-N,N-diisopropylamine or N-methylmorpholine, or potassium carbonate or sodium hydroxide.

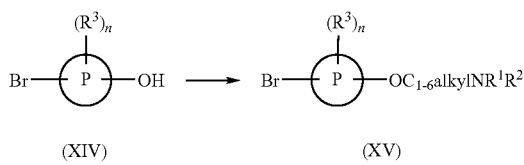

(XIV)                    (XV)

(xi) conversion of a compound of formula XIV, wherein R$^3$, n and P are as defined above, to obtain a compound of formula XV, wherein R$^1$, R$^2$, R$^3$, n and P are as defined above, may be carried out by reacting a compound of formula XIV with a suitable alcohol, R$^1$R$^2$NC$_{1-6}$alkylOH in the presence of triphenylphosphine and an appropriate azidodicarboxylate such as diethyl azidodicarboxylate. The reaction may be performed in a suitable solvent such as tetrahydrofuran, toluene or methylene chloride and at a reaction temperature between 0° C. to 60° C.

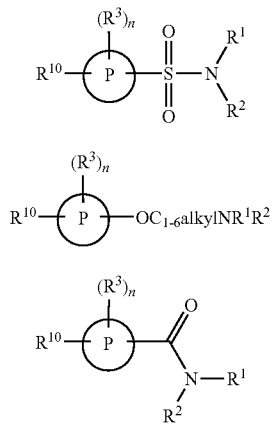

(XVIa)

(XVIb)

(XVIc)

(xii) borylation of compounds of formula XI, XIII and XV to compounds of formula XVIa-c (XVIa from XI, XVIb from XV and XVI from XIII), wherein P, R$^1$, R$^2$, R$^3$, C$_{1-6}$alkyl and n are as defined above and R$^{10}$ may be a group outlined in Scheme I, wherein R$^{11}$ and R$^{12}$ are C$_{1-6}$alkoxy or hydroxy, or C$_{1-3}$alkoxy fused together to form a 5 or 6 membered cyclic boron-oxygen-C$_{2-3}$alkyl species and the alkoxy, the aryl group or 5 or 6 membered cyclic boron-oxygen-C$_{2-3}$-alkyl species may be optionally substituted, may be carried out by a reaction with:

a) butyllithium or magnesium and a suitable boron compound such as trimethyl borate or triisopropyl borate. The reaction may be performed in a suitable solvent such as tetrahydrofuran, hexane or methylene chloride in a temperature range between $-78°$ C. and $+20°$ C.;

or, b) a palladium catalyst such as palladium tetrakis(triphenylphosphine), palladium diphenylphosphineferrocene dichloride or palladium acetate with or without a suitable ligand such as 2-(dicyclohexylphosphino)biphenyl, and a suitable boron species such as bis(catecholato)diboron, bis(pinacolato)diboron or pinacolborane. A suitable base, which under the reaction conditions do not promote dimerisation of compounds of formula XI, XIII and XV, such as a tertiary amine such as trietylamine or diisopropylethylamine or potassium acetate may be used. The reaction may be performed in a solvent such as dioxane, toluene or acetonitrile at temperatures between +80° C. and +100° C.

Scheme I.
Examples but not limations of R$^{10}$

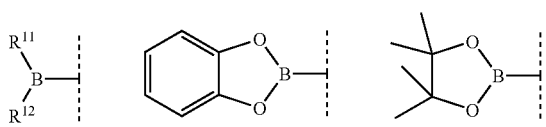

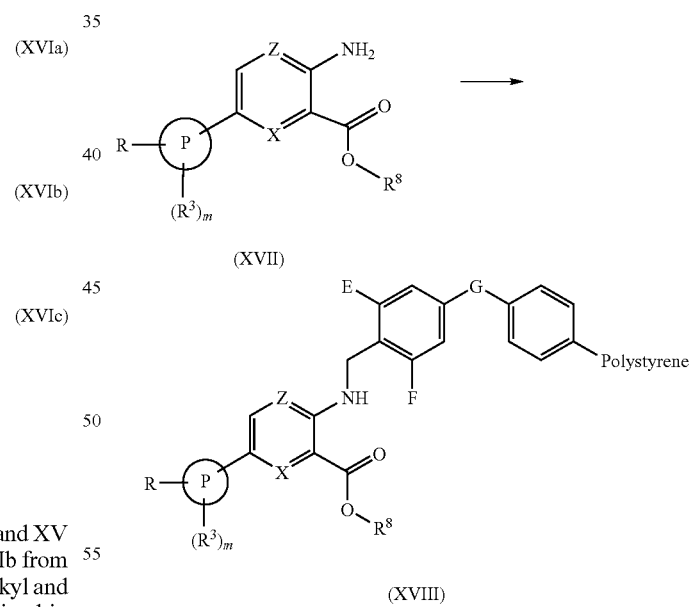

(xiii) conversion of a compound of formula XVII, wherein R$^8$ is C$_{1-6}$alkyl and R, R$^3$, P, X, Z and m are as defined above, to a compound of formula XVIII, wherein E and F are a methoxy group or hydrogen and G is a spacer chain containing atoms selected from oxygen and carbon, may be carried out by reaction with a suitable solid phase reagent such as a formyl polystyrene e.g. 2-(3,5-dimethoxy-4-formylphenoxy) ethyl polystyrene or 2-(4-formyl-3-methoxyphenoxy)ethyl polystyrene in a suitable solvents such as N,N-dimethylformamide or methylene chloride in the presence of a suitable acid e.g. acetic acid and a suitable reducing reagent such as sodium triacetoxyborohydride or sodium cyanoborohydride at a suitable reaction temperature ranging between 0° C. and +50° C. The reaction may be aided be the presence of trimethylsilyl chloride.

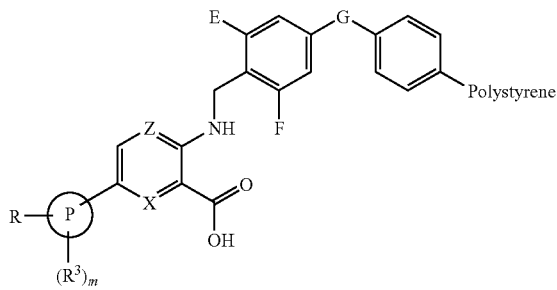

(XIX)

(xiv) hydrolysis of a compound of formula XVIII, wherein R, $R^3$, $R^8$, P, X, Z, and m are as defined above, and wherein E and F are a methoxy group or hydrogen and G is a spacer chain containing atoms selected from oxygen and carbon, to a compound of formula XIX may be carried out in a suitable solvent such as water, tetrahydrofuran or mixtures thereof in the presence of a suitable base such as sodium hydroxide, potassium hydroxide or lithium hydroxide at a suitable reaction temperature ranging between +25° C. and reflux.

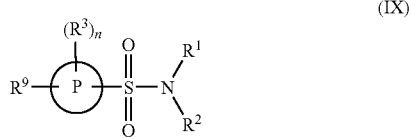

(IX)

(xv) conversion of a compound of formula IX, wherein $R^1$, $R^3$, P and n are as defined above and $R^2$ is $C_{1-6}$alkyl$OR^6$ where $R^6$ is hydrogen and $R^9$ is halogen e.g. bromine, or $NH_2$, to a compound of formula IX, wherein $R^1$, $R^3$, $R^9$, P and n are as defined above and $R^2$ is $C_{1-6}$alkyl$OR^6$ and $R^6$ is $C_{1-6}$alkyl, may be carried out in a suitable solvent such as methylene chloride or chloroform using a suitable reagent such as (trimethylsilyl)diazomethane in a reaction temperature between 0° C. and 20° C. The reaction may be aided by the use of a reagent such as fluoroboric acid.

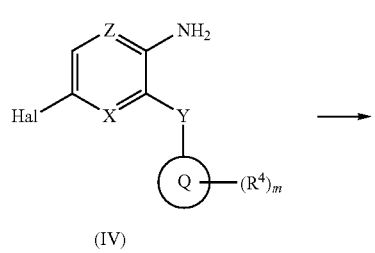

(IV)

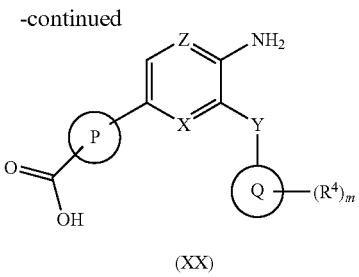

(XX)

(xvi) conversion of a compound of formula IV, wherein Z, X, Q, Y, $R^4$ and m are as defined above and Hal is halogen, to a compound of formula XX, wherein Z, X, Q, Y, $R^4$ and m are as defined above, may be carried out by the method described in (iv) using a compound of formula XXI, wherein P, $R^3$, $R^9$ and n are as defined above.

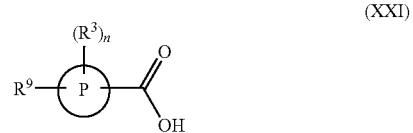

(XXI)

Methods of Preparation of the End Products

Another object of the invention are processes for the preparation of a compound of general formula I, wherein Y, X, Z, P, Q, R, $R^1$, $R^2$, $R^3$, $R^4$, $R^5$, $R^6$, $R^7$, A, m and n are, unless specified otherwise, defined as in formula I, comprising of:

A

De-halogen coupling, wherein $R^3$ and $R^4$ are substituents that are not susceptible to certain agents in the reaction, of a compound of formula IV with a appropriate aryl species to give a compound of formula I:

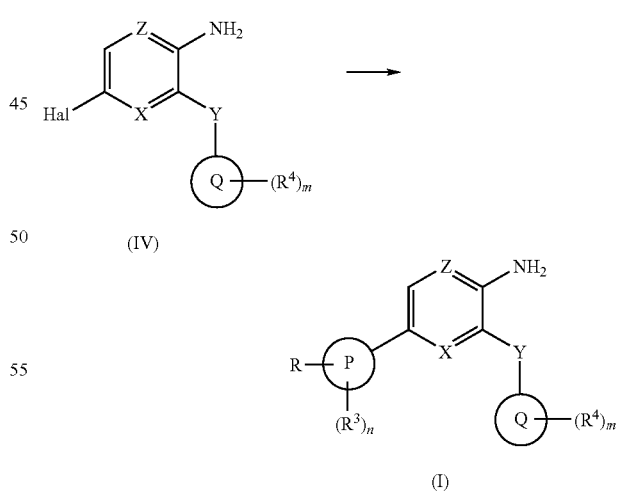

Thus, the de-halogen coupling according to process A may be carried out by coupling of a compound of formula IV with:

a) an appropriate aryl halogen such as aryl iodide, aryl bromide or aryl chloride in the presence of metals such as copper, nickel or zinc and nickel complexes, copper oxide or palladium acetate and tetrabutylammonium bromide and a base such as potassium carbonate or trietylamine. The reaction may occur at a temperature between 20° C. and 180° C. in a suitable solvent such as N,N-dimethylformamide, toluene or 2-pentanol;

or, b) an appropriate aryl boronic acid or a boronic ester such as compounds of formula XVIa-c (the boronic acid or boronic ester may be formed in situ using the compounds of formula XI, XIII and XV and conditions described in (xii)). The reaction may be carried out using a suitable palladium catalyst such as $Pd(PPh_3)_4$, $Pd(dppf)Cl_2$ or $Pd(OAc)_2$ with or without a suitable ligand such as $P(tert-butyl)_3$ in the presence of a suitable base such as an alkylamine e.g. triethylamine, or potassium carbonate, sodium carbonate, sodium hydroxide or cesium fluoride, which is performed in a temperature range between +20° C. and +160° C. using an oil bath or a microwave oven in a suitable solvent or solvent mixture such as toluene, tetrahydrofuran, ethylene glycol dimethyl ether/water, dimethoxyethane/water or N,N-dimethylformamide;

or, 2-(dicyclohexylphosphino)biphenyl or a nickel catalyst such as nickel on charcoal or $Ni(dppe)Cl_2$ together with Zn and sodium triphenylphosphinetrimetasulfonate. A suitable base such as an alkylamine e.g. triethylamine, or potassium carbonate, sodium carbonate, sodium hydroxide or cesium fluoride may be used in the reaction, which is performed in the temperature range between +20° C. and +160° C. using an oil bath or in a microwave oven in a suitable solvent or solvent mixture such as toluene, tetrahydrofuran, tetrahydrofuran/water, dimethoxyethane/water or N,N-dimethylformamide;

or, c) an appropriate aryl stannane in the presence of palladium catalyst such as $Pd(PPh_3)_4$, $Pd(PPh_3)_2Cl_2$ or $Pd(dba)_3$ and if needed a helping reagent such as 4-tert-butylcatechole, lithium chloride or potassium carbonate. Suitable solvents may be toluene, tetrahydrofuran or N,N-dimethylformamide. The reaction may occur in a temperature range of +20° C. and +120° C.;

or, d) an appropriate aryl halogen such as aryl iodide or aryl bromide by treatment with butyllithium in a suitable solvent such as tetrahydrofuran at a reaction temperature between −78° C. and −25° C., and a suitable base such as sodium carbonate or potassium carbonate in the presence of a suitable palladium catalyst such as $Pd(dppf)Cl_2$ or $Pd(OAc)_2$ and at a reaction temperature between 25° C. and reflux.

B

Amidation, wherein $R^3$ and $R^4$ are substituents that are not susceptible to certain agents in the reaction, of a compound of formula VI with the appropriate amine:

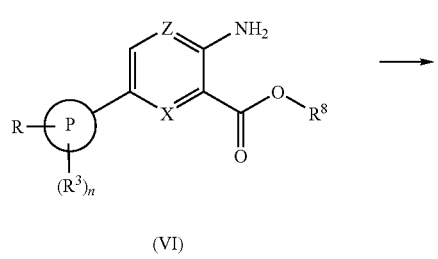

(VI)

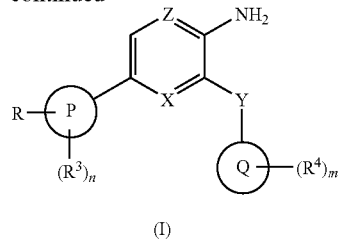

(I)

Thus, the amidation according to process B may be carried out by treating a compound of formula VI, wherein $R^8$ is $C_{1-6}$alkyl, with the appropriate amine such as a compound of formula V. The reaction can be performed neat or using a suitable solvent such as N,N-dimethylformamide, acetonitrile, methylene chloride or ethyl acetate at a temperature ranging from −25° C. to +150° C. The reaction may be aided by using a base such as potassium carbonate, triethylamine or 1,8-diazabicyclo[5.4.0]undec-7-ene or an acid such as trimethylaluminum or p-toulenesulfonic acid;

or, the amidation of a compound of formula VI, wherein $R^8$ is hydrogen, may be performed by activation of a compound of formula VI by treating the compound with coupling reagents such as 1,3-diisopropylcarbodiimide, 1-[3-(dimethylamino) propyl]-3-ethylcarbodiimide hydrochloride, 1,3-dicyclohexylcarbodiimide, O-(benzotriazol-1-yl)-N,N,N',N'-tetramethyluronium tetrafluoroborate, O-(benzotriazol-1-yl)-N,N,N',N'-tetramethyluronium hexafluorophosphate, 1,1'-carbonyldiimidazole or O-(7-azabenzotriazol-1-yl)-N,N,N', N'-tetramethyluronium hexafluorophosphate where the reaction may be aided by the addition of 1-hydroxybenzotriazole hydrate, or using an acyl halide reagent such as cyanuric chloride, oxalyl chloride, thionyl chloride or bromotrispyrrolidinophosphonium hexafluorophosphate followed by treatment with the appropriate amine such as a compound of formula V in a suitable solvent such as methylene chloride chloroform, N,N-dimethylformamide, acetonitrile, tetrahydrofuran or mixtures thereof and at a reaction temperature between 0° C. and reflux. The reaction may be aided by using a base such as potassium carbonate or a trialkylamine e.g triethylamine or N-ethyl-N,N-diisopropylamine

C

Amidation, wherein $R^3$ and $R^4$ are substituents that are not susceptible to certain agents in the reaction, of a compound of formula XX, with the appropriate amine to give a compound of formula I:

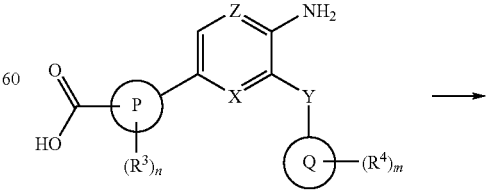

(XX)

-continued

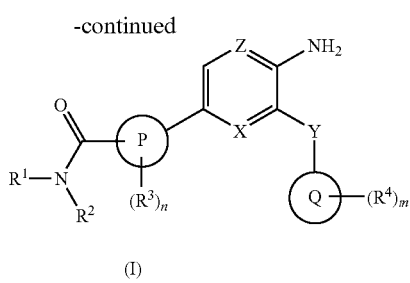

(I)

Thus the amidation of a compound of formula XX according to process C may be performed by activation of the carboxylic acid function in a compound of formula XX, by treating the compound with coupling reagents such as 1,3-diisopropylcarbodiimide, 1-[3-(dimethylamino)propyl]-3-ethylcarbodiimide hydrochloride, 1,3-dicyclohexylcarbodiimide, O-(benzotriazol-1-yl)-N,N,N',N'-tetramethyluronium tetrafluoroborate, O-(benzotriazol-1-yl)-N,N,N',N'-tetramethyluronium hexafluorophosphate, 1,1'-carbonyldiimidazole or O-(7-azabenzotriazol-1-yl)-N,N,N',N'-tetramethyluronium hexafluorophosphate where the reaction may be aided by the addition of 1-hydroxybenzotriazole hydrate, or using an acyl halide reagent such as cyanuric chloride, oxalyl chloride, thionyl chloride or bromotrispyrrolidinophosphonium hexafluorophosphate in a suitable solvent such as N,N-dimethylformamide, methylene chloride, methanol, dioxane or tetrahydrofuran followed by treatment with the appropriate amine $HNR^1R^2$ and at a reaction temperature between 25° C. and 70° C.

D

Amidation, wherein $R^3$ and $R^4$ are substituents that are not susceptible to certain agents in the reaction, of a compound of formula XIX with the appropriate amine:

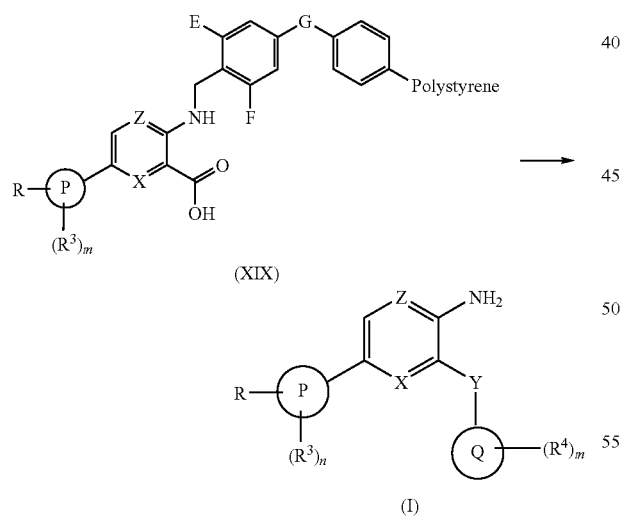

Thus, the amidation of a compound of formula XIX, may be performed by activation of a compound of formula XIX by treating the compound with coupling reagents such as 1,3-diisopropylcarbodiimide, 1-[3-(dimethylamino)propyl]-3-ethylcarbodiimide hydrochloride, 1,3-dicyclohexylcarbodiimide, O-(benzotriazol-1-yl)-N,N,N',N'-tetramethyluronium tetrafluoroborate, O-(benzotriazol-1-yl)-N,N,N',N'-tetramethyluronium hexafluorophosphate, 1,1'-carbonyldiimidazole or O-(7-azabenzotriazol-1-yl)-N,N,N',N'-tetramethyluronium hexafluorophosphate where the reaction may be aided by the addition of 1-hydroxybenzotriazole hydrate, or using an acyl halide reagent such as cyanuric chloride, oxalyl chloride, thionyl chloride or bromotrispyrrolidinophosphonium hexafluorophosphate followed by treatment with the appropriate amine such as a compound of formula V in a suitable solvent such as methylene chloride chloroform, N,N-dimethylformamide, acetonitrile or tetrahydrofuran and at a reaction temperature between 0° C. and reflux. The reaction may be aided by using a base such as potassium carbonate or a trialkylamine e.g triethylamine or N-ethyl-N,N-diisopropylamine, followed by, cleavage of the solid phase moiety by treatment with an suitable acid such as trifluoroacetic acid in a suitable solvent such as methylene chloride or chloroform and at a reaction temperature between 0° C. and reflux to give the compound of formula (I).

The hydrochloric salt of compound of formula I may be obtained from a compound of formula I by treatment with hydrochloric acid at a temperature range between 0° C. and +25° C., in suitable solvent such as methylene chloride, tetrahydrofuran or methylene chloride/methanol mixture.

WORKING EXAMPLES

Example 1

3-Amino-6-bromo-N-pyridin-3-ylpyrazine-2-carboxamide

To 3-aminopyridine (10 g, 106 mmol) at 70° C. were added methyl 3-amino-6-bromo-2-pyrazinecarboxylate (1.0 g, 4.3 mmol) and 1,8-diazabicyclo[5.4.0]undec-7-ene (645 µL, 4.3 mmol). The reaction solution was stirred for 4 h, diluted with water (75 mL) and extracted with methylene chloride. The combined organic layers were washed with a saturated ammonium chloride solution, dried ($MgSO_4$), filtered and evaporated in vacuo. The crude product was purified on a silica gel column using methylene chloride/ethanol, (9:1), as the eluent to give 750 mg (59% yield) of the title compound as a yellow solid: $^1$H NMR ($CDCl_3$, 400 MHz) δ 9.50 (br s, 1H) 8.82 (d, J=3 Hz, 1H), 8.43 (dd, J=5 and 1 Hz, 1H), 8.31 (s, 1H), 8.23 (ddd, J=8, 3 and 2 Hz, 1H), 7.34 (dd, J=8, 5 Hz, 1H); MS (TSP) m/z 294 ($M^+$+1).

Example 2

1-[(4-Bromophenyl)sulfonyl]pyrrolidine

Pyrrolidine (2.5 g, 35.2 mmol) was added to a solution of 4-bromobenzenesulfonyl chloride (4.5 g, 17.6 mmol) in methylene chloride (10 mL) at 0° C. The mixture was stirred for 2 h and an aqueous sodium hydroxide solution (1 M, 5 mL) was added and sting was continued for another 10 min. The organic phase was separated and diluted with methylene chloride (40 mL), washed with aqueous HCl (1 M, 10 mL), and water (2×10 mL). The organic phase was dried (sodium sulfate) and the solvent was evaporated. The title compound was isolated in 5.0 g (98% yield) as a white solid: $^1$H NMR ($CDCl_3$, 400 MHz) δ 7.65 (m, 4H), 3.20 (m, 4H), 1.74 (m, 4H); $^{13}$C NMR (CDCl$_3$, 100 MHz) δ 135.93, 132.17, 128.84, 127.39, 47.84, 25.13; MS (ES) m/z 290 and 292 (M$^+$+1).

Example 3

4-(Pyrrolidin-1-ylsulfonyl)phenylboronic Acid n-Butyllithium (20 mL, 31 mmol) was added dropwise over 30 min to a cooled (−78° C.) solution of 1-[(4-bromophenyl)sulfonyl]pyrrolidine (3.0 g, 10.3 mmol) and triisopropyl borate (7.2 mL, 30.9 mol) in anhydrous tetrahydrofuran (10 mL) under a nitrogen atmosphere. The reaction mixture was stirred for 1 h at −78° C. whereafter the temperature was allowed to reach room temperature over 3 h. Silica gel was added and the solvent was evaporated. Chromatography on a silica gel column using a gradient methylene chloride (100%) to methylene chloride/ethanol, (1:1), gave 1.85 g (70% yield) of the title compound as a white solid: $^1$H NMR (CD$_3$OD, 400 MHz) δ 7.90 (d, J=7 Hz, 2H), 7.75 (d, J=8 Hz, 2H), 3.21 (m, 4H), 1.72 (m, 4H); $^{13}$C NMR (CDCl$_3$/CD$_3$OD (1:1), 100 MHz) δ 136.79, 133.50, 125.48, 47.19, 24.30; MS (ES) m/z 256 (M$^+$+1).

Example 4

4-Bromo-N-[(1R)-2-hydroxy-1-methylethyl]benzenesulfonamide (2R)-2-Aminopropan-1-ol (2.0 g, 26.7 mmol) and N-ethyl-N,N-diisopropylamine (8.5 mL, 48.9 mmol) was added dropwise over 20 min to a cooled (0° C.) solution of 4-bromobenzenesulfonyl chloride (6.12 g, 24 mmol) in methylene chloride (20 mL). The reaction mixture was allowed to stir for 1 h. Water was added and the mixture was washed, twice, with HCl (aq, 1 M) and one time with saturated aqueous sodium hydrogen carbonate. The organic phase was dried over sodium sulfate and evaporated to give 6.8 g, (96% yield) of the title compound: $^1$H NMR (CD$_3$OD, 400 MHz) δ 7.82 (d, J=8 Hz, 2H), 7.76 (d, J=8 Hz, 2H), 3.44 (m, 1H), 3.34 (m, 3H), 1.03 (d, J=7 Hz, 3H); MS (ESI) m/z (M$^+$+1); $^{13}$C NMR (CD$_3$OD, 100 MHz) 142.42, 133.36, 129.74, 127.90, 66.81, 52.49, 17.94

Example 5

4-Bromo-N-[(1R)-2-methoxy-1-methylethyl]benzenesulfonamide (Trimethylsilyl)diazomethane (10 mL, 10 mmol) was added to a vigorously stirred mixture of 4-bromo-N-[(1R)-2-hydroxy-1-methylethyl]benzenesulfonamide (1.0 g, 3.4 mmol) and aqueous fluoroboric acid (conc. 42%, 6.8 mmol) in methylene chloride (25 mL), in 5 portions over 1 h at 0° C. The stirring was continued at 0° C. and another portion of trimethylsilyldiazomethane (5 mL, 5 mmol) was added over 30 min. The stirring was continued for 30 min, poured into water and extracted with methylene chloride. The organic phase was washed with water, dried over sodium sulfate and concentrated. Purification by column chromatography using gradient heptane to heptane/ethylacetate, (2:1), as the eluent gave 0.155 g (15% yield) of the title compound: MS (ESI) 309 m/z (M$^+$+1).

Example 6

4-Bromo-N-[(1S)-2-methoxy-1-methylethyl]benzenesulfonamide (1S)-2-Methoxy-1-methylethylamine (7.34 g, 82.4 mmol) and N-ethyl-N,N-diisopropylamine (19.1, 110 mmol) was added dropwise over 20 min to a cooled (0° C.) solution of 4-bromobenzenesulfonyl chloride (14.0 g, 55 mmol) in methylene chloride (200 mL). The reaction mixture was allowed to stir for 1 h. Water was added and the mixture was washed, twice, with HCl (1 M) and once with saturated aqueous sodium hydrogen carbonate. The organic phase was dried over sodium sulfate and evaporated to give 15.1 g, (94% yield) of the title compound: $^1$H NMR (CDCl$_3$, 400 MHz) δ 7.76 (d, J=8 Hz, 2H), 7.65 (d, J=8 Hz, 2H), 4.97 (m, 1H), 3.46 (m, 1H), 3.23 (m, 5H), 1.12 (d, J=7 Hz, 3H); MS (ESI) m/z 308 and 310 (M$^+$+1)

Example 7

Methyl 3-amino-6-[4-(pyrrolidin-1-ylsulfonyl)phenyl]pyrazine-2-carboxylate 4-(Pyrrolidin-1-ylsulfonyl)phenylboronic acid (0.33 g, 1.29 mmol), methyl 3-amino-6-bromopyrazine-2-carboxylate (0.25 g, 1.08 mmol; described in: H. Ellingson, J. Amer. Chem. Soc. 1949, 2798), K$_3$PO$_4$ (3 M, 1.1 mL, 3.2 mmol), and Pd(dppf)Cl$_2$ (0.044 g, 54 µmol) were suspended in ethylene glycol dimethyl ether/water (1.5:0.5 mL) and heated in a microwave oven at 160° C. for 10 min. The reaction was repeated 3 times. The combined product mixtures were evaporated with silica gel and the crude product was purified by chromatography on silica gel using a heptane to ethyl acetate gradient to give 0.96 g (82% yield) of the title compound: MS (ES) m/z 363 (M$^+$+1).

Example 8

4-[(4-Methylpiperazin-1-yl)sulfonyl]phenylboronic Acid

Triisopropyl borate (0.64 mL, 2.8 mmol) was added to a solution of 1-[(4-bromophenyl)sulfonyl]-4-methylpiperazine (0.602 g, 1.9 mmol; described in: Keasling, H. H. et el. J. Med. Chem. 1965, 8, 548-550) in anhydrous tetrahydrofuran (7 mL) at −78° C. under a nitrogen atmosphere followed by dropwise addition of n-butyllithium (1.4 mL, 2.2 mmol). The resulting mixture was stirred at −78° C. for 2 h and at room temperature for another 16 h. Water (2.0 mL) was added and the mixture stirred for 30 min and evaporated to dryness. The residue was pre-adsorbed onto silica and purified by column chromatography using methylene chloride/methanol, (9:1 to 1:9), as the eluent. The product was re-crystallized from water to give 311 mg (58% yield) of the title compound as white crystals: mp 215-218° C.; $^1$H NMR (DMSO-d6, 400 MHz) δ 10.89 (br s, 1H), 8.47 (br s, 2H), 8.05 (d, J=8 Hz, 2H), 7.73 (d, J=8 Hz, 2H), 3.77 (m, 2H), 3.40 (m, 2H), 3.13 (m, 2H), 2.71 (s, 3H), 2.65 (m, 2H); $^{13}$C NMR (DMSO-d6, 100 MHz) δ 133.7, 133.3, 124.7, 49.8, 41.6, 41.4; MS (TSP) m/z 285 (M$^+$+1).

Example 9

Methyl 3-amino-6-[4-[(4-methyl-1-piperazinyl)sulfonyl]phenyl]pyrazine-2-carboxylate Triisopropyl borate (2.7 mL, 11.6 mmol) was added to a solution of 1-[(4-bromophenyl)sulfonyl]-4-methylpiperazine in (1.24 g, 3.87 mmol; described: in Keasling, H. H. et el. *J. Med. Chem.* 1965, 8, 548-550) in anhydrous tetrahydrofuran (25 mL) at −78° C. under an atmosphere of nitrogen, followed by dropwise addition of n-butyllithium (9.8 mL, 15.5 mmol). The resulting mixture was stirred at −78° C. for 30 min, then allowed to warm to room temperature. HCl (3 M aq, 7.8 mL, 23.2 mmol) was added and the mixture was stirred at room temperature for 10 min. Sodium carbonate (4.1 g, 38.7 mmol) was added followed by the addition of methyl 3-amino-6-bromo-2-pyrazinecarboxylate (0.79 g, 3.4 mmol; described in: H. Ellingson, *J. Amer. Chem. Soc.* 1949, 2798) and Pd(dppf)Cl$_2$ (95 mg, 0.12 mmol). The resulting mixture was heated at 55° C. overnight. Silica was added, the solvent was evaporated and the crude mixture was purified by column chromatography on silica using chloroform/methanol, (99:1), as the eluent to give 0.923 g (69% yield) of the base as a yellow solid: 1HNMR (DMSO-d$_6$) δ 9.0 (s, 1H), 8.22 (d, J=7 Hz, 2H), 7.80 (d, J=7 Hz, 2H), 7.62 (br s, 2H), 3.90 (s, 3H) 2.91 (m, 4H), 2.36 (m, 4H), 2.12 (s, 3H); $^{13}$C NMR (DMSO-d$_6$) δ 166.2, 155.1, 145.8, 140.33, 127.5, 134.0, 128.1, 125.7, 109.1, 53.5, 52.3, 45.7, 45.2; MS (ESP) m/z 392 (M$^+$+1).

Example 10

3-Amino-6-[4-[(4-methyl-1-piperazinyl)sulfonyl]phenyl]-2-pyrazinecarboxylic Acid Methyl 3-amino-6-[4-[(4-methyl-1-piperazinyl)sulfonyl]phenyl]pyrazine-2-carboxylate was dissolved in anhydrous tetrahydrofuran (10 mL). Lithium hydroxide (0.113 g, 4.72 mmol) in water (19 mL) was added at room temperature and the resulting mixture was stirred at 50° C. for 3 h. The tetrahydrofuran was evaporated and the pH of the water phase was adjusted to 6 with HCl (aq). The precipitated product was filtered and washed with water and dried to give 0.763 g (86% yield) of the title compound as a pale yellow solid: $^1$HNMR (TFA) δ 8.83 (s, 2H), 8.23 (m, 2H), 7.97 (m, 2H), 4.09 (m, 2H), 3.76 (m, 2H), 2.25 (m, 2H), 3.04 (m, 5H); $^{13}$CNMR (TFA) δ 165.81, 147.39, 139.5, 139.2, 135.7, 132.1, 131.1, 128.5, 127.3, 53.9, 43.5, 43.2; MS (ESP) m/z 378 (M$^+$+1).

Example 11

4-[2-(4-Bromo-2-fluorophenoxy)ethyl]morpholine

A mixture of 4-bromo-2-fluorophenol (0.612 g, 3.2 mmol; described: in Finger et al. *J. Amer. Chem. Soc.* 1959, 81, 94), 4-(2-hydroxyethyl)morpholine (0.47 ml, 3.84 mmol) and triphenylphosphine (1.0 g, 3.84 mmol) was dissolved in anhydrous tetrahydrofuran (5 mL) and cooled to 0° C. Diethyl azodicarboxylate (0.6 mL, 3.84 mmol) was added dropwise and the resulting mixture was stirred at room temperature for 3.5 h. The solvent was evaporated and the residue partioned between water and methylene chloride. The organic phase was washed twice with a saturated sodium hydrogen carbonate solution, dried (MgSO$_4$) and the solvent was evaporated. The product was purified by column chromatography on silica using a gradient of toluene/acetonitrile, (4:1 to 0:1), as the eluent to give 0.655 g (67% yield) of the title compound as a clear oil: $^1$H NMR (CDCl$_3$) δ 7.21 (d, J=11 Hz, 1H), 7.16 (m, 1H), 6.83 (t, J=9 Hz, 1H), 4.14 (t, J=6 Hz, 3H), 3.71 (t, J=5 Hz, 4H), 2.80 (t, J=6 Hz, 2H), (t, J=5 Hz, 4H); $^{13}$C NMR (CDCl$_3$, 100) δ 154.2, 151.7, 146.5, 146.4, 127.4, 127.4, 120.1, 119.9, 116.8, 116.8, 112.7, 112.7, 68.1, 67.1, 57.6, 54.3; MS (ESP) m/z 304, 306 (M$^+$+1).

Example 12

4-Bromo-N-(1-ethyl-3-piperidinyl)benzenesulfonamide

3-Amino-1-ethylpiperidine (0.4 mL, 3.13 mmol) was added to a solution of 4-bromo-benzenesulfonyl chloride (0.4 g, 1.56 mmol) in methylene chloride (10 mL) at room temperature. The mixture was stirred overnight. The reaction solution was extracted three times with a aqueous saturated sodium hydrogen carbonate solution, dried (MgSO$_4$) and evaporated to give 0.533 g (93% yield) of the title compound as a light brown solid: $^1$H NMR (CDCl$_3$) δ 7.74 (d, J=9 Hz, 2H), 7.62 (d, J=9 Hz, 2H), 3.45 (br s, 1H), 2.46 (br s, 1H), 2.27 (m, 2H), 2.23 (m, 2H), 2.13 (m, 1H), 1.64 (m, 1H), 1.45 (m, 3H), 0.93 (t, J=7 Hz, 3H); $^{13}$C NMR (CDCl$_3$) δ 140.7, 132.5, 128.7, 127.5, 53.2, 52.3, 49.7, 21.9, 12.1; MS (ESP) m/z 347, 349 (M$^+$+1).

The following Examples, 13-14, were synthesized as described for Example 12:

Example 13

4-Bromo-N,N-bis(2-methoxyethyl)benzenesulfonamide

Starting materials: bis(2-methoxyethyl)amine and 4-bromobenzenesulfonyl chloride. Yield: 99% as a yellow oil: $^1$H NMR (CDCl$_3$) δ 7.69 (d, J=9 Hz, 2H), δ 7.62 (d, J=9 Hz, 2H), 3.49 (m, 4H), 3.39 (m, 4H), 3.27 (s, 6H); MS (ESP) m/z 352, 354 (M$^+$+1).

Example 14

4-bromo-N-(3-methylbutyl)-benzenesulfonamide

Starting materials: isoamylamine and 4-bromobenzenesulfonyl chloride. Yield 98% as a white solid: $^1$H NMR (CDCl$_3$) δ 7.71 (d, J=9 Hz, 2H), 7.62 (d, J=9 Hz, 2H), 4.26 (br s, 1H), 2.82 (t, J=7 Hz, 2H), 1.52 (m, 1H), 1.30 (q, J=7 Hz, 2H), 0.86 (s, 3H), 0.84 (s, 3H); $^{13}$C NMR (CDCl$_3$) δ 139.3, 132.6, 128.8, 127.7, 41.7, 38.6, 25.6, 22.8, 22.4; MS (ESP) m/z 306, 308 (M$^+$+1).

Example 15

Methyl 3-{[2,6-dimethoxy-4-(2-phenylethoxy)benzyl]amino}-6-[4-(pyrrolidin-1-ylsulfonyl)phenyl]pyrazine-2-carboxylate Polystyrene Sodium triacetoxyborohydride (2.6 g, 12.2 mmol) in N,N-dimethylformamide/acetic acid (98:2, 20 mL) and trimethylsilyl chloride (1.17 mL, 9.18 mmol) were added to a mixture of methyl 3-amino-6-[4-(pyrrolidin-1-ylsulfonyl)phenyl]pyrazine-2-carboxylate (4.4 g, 12.2 mmol) and 2-(3,5-dimethoxy-4-formylphenoxy)ethyl polystyrene (12 g, 0.51 mmol/g) in N,N-dimethylformamide (60 mL). The mixture was shaken for 3 h and then filtered. The polystyrene resin was washed, three times, with N,N-dimethylformamide and three times with methylene chloride. The procedure was repeated using sodium triacetoxyborohydride (2.6 g, 12.24 mmol) in N,N-dimethylformamide/acetic acid, (98:2, 20 mL), trimethylsilyl chloride (1.17 ml, 9.18 mmol) and methyl 3-amino-6-[4-(pyrrolidin-1-ylsulfonyl)phenyl]pyrazine-2-carboxylate (12 g, 0.51 mmol/g) and shaking was continued for 18 h. The polystyrene resin was washed, three times, with N,N-dimethylformamide, three times with dichloromethane and three times with methanol. The resin was dried under vacuum and gave 12.5 g of the title compound.

Analysis: The title compound (50 mg) was treated with trifluoroacetic acid in dichloromethane (conc. 95%) for 30 min, filtered and the solvent was analyzed by MS: MS (ESI) 363 m/z (M$^+$+1) (which corresponds to the starting material).

Example 16

3-{[2,6-Dimethoxy-4-(2-phenylethoxy)benzyl]amino}-6-[4-(pyrrolidin-1-ylsulfonyl)phenyl]pyrazine-2-carboxylic Acid Polystyrene A solution of lithium hydroxide (4 M, 10 mL) was added to a suspension of methyl 3-{[2,6-dimethoxy-4-(2-phenylethoxy)benzyl]amino}-6-[4-(pyrrolidin-1-ylsulfonyl)phenyl]pyrazine-2-carboxylate polystyrene (12 g, 0.51 mmol/g) in tetrahydrofuran (100 mL). The mixture was shaken for 17 h. Filtering and washing of the resin three times with N,N-dimethylformamide/water, (4:1), and three times with N,N-dimethylformamide/acetic acid, (98:2,) and three times with methanol and drying of the resin gave 11.8 g of the title compound.

Analysis: The title compound (50 mg) was treated with trifluoroacetic acid in dichloromethane (conc. 95%) for 30 min, filtered and the solvent was analyzed by MS: MS (ESI) 349 m/z (M$^+$+1).

Example 17

3-Amino-6-[4-({[(1R)-2-methoxy-1-methylethyl]amino}sulfonyl)phenyl]-N-pyridin-3-ylpyrazine-2-carboxamide Hydrochloride n-Butyllithium (1.3 mL, 2.1 mmol) was added dropwise over 30 min to a cooled (−78° C.) solution of 4-bromo-N-[(1R)-2-methoxy-1-methylethyl]benzenesulfonamide (0.125 g, 0.406 mmol) and triisopropyl borate (0.28 mL, 1.2 mmol) in anhydrous tetrahydrofuran (10 mL) under nitrogen atmosphere. The reaction mixture was stirred for 2 h at −78° C. HCl (aq, 3 M, 0.81 mL) was added to the reaction mixture and the mixture was allowed to warm to room temperature. Sodium carbonate (0.516 g, 4.9 mmol) was added followed by Pd(dppf)Cl$_2$ (16 mg, 20 μmol) and 3-amino-6-bromo-N-pyridin-3-ylpyrazine-2-carboxamide (0.143 g, 0.487 mmol). Tetrahydrofuran (10 mL) was added and the mixture was heated to 65° C. for 15 h. The solvent was removed and purification by column chromatography using gradient methylene chloride to methylene chloride/methanol, (2:1), as the eluent gave a yellow solid. The solid was dissolved in methylene chloride (10 mL) and HCl in diethyl ether (1 M 2.5 ml) was added. A yellow precipitate was formed. Filtering and drying gave 73 mg (35% yield) of the title compound as yellow solid: $^1$H NMR (D$_2$O, 400 Hz) δ 9.28 (s, 1H), 8.53 (s, 3H), 8.0 (m, 1H), 7.96 (d, J=8 Hz, 2H), 7.70 (d, J=8 Hz, 2H), 3.42 (m, 1H), 3.27 (m, 1H), 3.16 (s, 3H), 0.93 (d, J=7 Hz, 3H);

Example 18

3-Amino-6-[4-({[(1S)-2-methoxy-1-methylethyl]amino}sulfonyl)phenyl]-N-pyridin-3-ylpyrazine-2-carboxamide Hydrochloride The title compound was prepared as described for Example 17 using 4-bromo-N-[(1S)-2-methoxy-1-methylethyl]benzenesulfonamide. Yield: 77% of the title compound as yellow solid: $^1$H NMR (D$_2$O, 400 Hz) δ 9.27 (s, 1H), 8.53 (m, 3H), 8.0 (d, J=8 Hz, 2H), 7.99 (m, 1H), 7.70 (d, J=8 Hz, 2H), 3.42 (m, 1H), 3.26 (d, m, 2H), 3.25 (s, 3H), 0.92 (d, J=6 Hz, 3H); MS (ESI) 443 m/z (M$^+$+1).

Example 19

3-Amino-N-(3-nitrophenyl)-6-[4-(pyrrolidin-1-ylsulfonyl)phenyl]pyrazine-2-carboxamide 3-Nitroaniline (70 mg, 0.51 mmol), O-(benzotriazol-1-yl)-N,N,N',N'-tetramethyluronium tetrafluoroborate (0.164 g, 0.51 mmol) and 1-hydroxybenzotriazole hydrate (69 mg, 0.51 mmol) were added to 3-{[2,6-dimethoxy-4-(2-phenylethoxy)benzyl]amino}-6-[4-(pyrrolidin-1-ylsulfonyl)phenyl]pyrazine-2-carboxylic acid polystyrene (0.50 g, 0.51 mmol/g, 0.255 mmol) in N,N-dimethylformamide (2 mL). The mixture was shaken for 5 min where after N-ethyl-N,N-diisopropylamine (0.133 mL, 0.765 mmol) was added. The mixture was shaken for 18 h, filtered and washed N,N-dimethylformamide and three times with methylene chloride. The product was isolated by treating the resin with trifluoroacetic acid in methylene chloride (conc. 95%) for 30 min and then filtered. The solution was evaporated and purification by preparative HPLC (column: XTerra C8 19×300 mm, eluent: gradient acetonitrile/water, (20:80 to 80:20)), gave 3.1 mg (1.3% yield) of the title compound: $^1$H NMR (CDCl$_3$, 400 MHz) δ 8.60 (s, 1H), 7.99 (m, 3H), 7.80 (m, 3H), 7.50 (d, J=8 Hz, 2H), 7.38 (t, J=8 Hz, 1H), 3.15 (m, 4H), 1.68 (m, 4H); MS (ESI) 439 m/z (M$^+$+1).

Example 20

3-Amino-6-[4-(pyrrolidin-1-ylsulfonyl)phenyl]-N-1H-tetrazol-5-ylpyrazine-2-carboxamide The title compound was prepared as described Example 19 using 1H-tetrazol-5-amine.

Yield: 1.1%: MS (ESI) 416 m/z (M$^+$+1).

Example 21

3-Amino-N-(2-methoxyphenyl)-6-{4-[(4-methylpiperazin-1-yl)sulfonyl]phenyl}pyrazine-2-carboxamide Hydrochloride 2-Methoxyaniline (80 mg, 318 mmol) was added to a mixture of 3-amino-6-[4-[(4-methyl-1-piperazinyl)sulfonyl]phenyl]-2-pyrazinecarboxylic acid (80 mg, 212 mmol), O-(benzotriazol-1-yl)-N,N,N',N'-tetramethyluronium tetrafluoroborate (82 mg, 255 mmol), 1-hydroxybenzotriazole hydrate (34 mg, 255 mmol) and N-ethyl-N,N-diisopropylamine (0.111 mL, 0.637 mmol) in N,N-dimethylformamide (2 mL). The reaction mixture was stirred for 13 h. The reaction was quenched with water (1 mL) and the solvent was evaporated. Purification by preparative HPLC (column: XTerra C8 19×300 mm, eluent: a acetonitrile/water, (20:80 to 80:20), gradient) followed by evaporation of the solvent gave a yellowish solid that was dissolved in methylene chloride (10 mL). HCl in diethyl ether (1 M, 2.5 mL) was added while stirring. Filtration and drying gave 12 mg (12% yield) of the title compound: MS (ESI) 483 m/z (M$^+$+1).

The following Examples, 22-30, were synthesized as described for Example 21:

Example 22

3-Amino-N-(4-methoxyphenyl)-6-{4-[(4-methylpiperazin-1-yl)sulfonyl]phenyl}pyrazine-2-carboxamide Hydrochloride Starting material: 4-methoxyaniline. Yield: 62%: MS (ESI) 483 m/z (M$^+$+1).

Example 23

3-Amino-N-[2-(aminocarbonyl)phenyl]-6-{4-[(4-methylpiperazin-1-yl)sulfonyl]phenyl}pyrazine-2-carboxamide Hydrochloride Starting material: 2-aminobenzamide. Yield: 19%: MS (ESI) 496 m/z (M$^+$+1).

Example 24

3-Amino-N-[3-(aminocarbonyl)phenyl]-6-{4-[(4-methylpiperazin-1-yl)sulfonyl]phenyl}pyrazine-2-carboxamide Hydrochloride Starting material: 3-aminobenzamide. Yield: 49%: MS (ESI) 496 m/z (M$^+$+1).

Example 25

3-Amino-N-(3-cyanophenyl)-6-{4-[(4-methylpiperazin-1-yl)sulfonyl]phenyl}pyrazine-2-carboxamide Hydrochloride Starting material: 3-aminobenzonitrile. Yield: 19%: MS (ESI) 478 m/z (M$^+$+1).

Example 26

3-Amino-N-(2-bromophenyl)-6-{4-[(4-methylpiperazin-1-yl)sulfonyl]phenyl}pyrazine-2-carboxamide Hydrochloride Starting material: 2-bromoaniline. Yield: 20%: MS (ESI) 531, 533 m/z (M$^+$+1).

Example 27

3-Amino-N-(3-bromophenyl)-6-{4-[(4-methylpiperazin-1-yl)sulfonyl]phenyl}pyrazine-2-carboxamide Hydrochloride Starting material: 3-bromoaniline. Yield: 2.3%: MS (ESI) 531, 533 m/z (M$^+$+1).

Example 28

3-Amino-6-{4-[(4-methylpiperazin-1-yl)sulfonyl]phenyl}-N-1H-pyrazol-3-ylpyrazine-2-carboxamide Hydrochloride Starting material: 1H-pyrazol-3-amine. Yield: 36%: MS (ESI) 443 m/z (M$^+$+1).

Example 29

3-Amino-N-[4-(aminocarbonyl)-1H-pyrazol-3-yl]-6-{4-[(4-methylpiperazin-1-yl)sulfonyl]phenyl}pyrazine-2-carboxamide Hydrochloride Starting material: 3-amino-1H-pyrazole-4-carboxamide. Yield: 36%: MS (ESI) 486 m/z (M$^+$+1).

Example 30

3-Amino-N-1H-imidazol-2-yl-6-{4-[(4-methylpiperazin-1-yl)sulfonyl]phenyl}pyrazine-2-carboxamide Hydrochloride Starting material: 1H-imidazol-2-amine. Yield: 5%: MS (ESI) 443 m/z (M$^+$+1).

Example 31

3-Amino-6-[3-fluoro-4-[2-(4-morpholinyl)ethoxy]phenyl]-N-3-pyridinyl-2-pyrazinecarboxamide Hydrochloride Triisopropyl borate (0.91 mL, 3.96 mmol) was added to a solution of 4-[2-(4-bromo-2-fluorophenoxy)ethyl]morpholine (0.402 g, 1.32 mmol) in anhydrous tetrahydrofuran (10 mL) at −78° C. under an atmosphere of nitrogen, followed by dropwise addition of n-butyllithium (2.5 mL, 3.96 mmol) over 5 min. The resulting mixture was stirred at −78° C. for 50 min then allowed to warm to room temperature. HCl (3 M aq, 2.2 mL, 6.61 mmol) was added and the mixture was stirred at room temperature for 10 min. Sodium carbonate (1.40 g, 13.2 mmol) was added followed by the addition of 3-amino-6-bromo-N-pyridin-3-ylpyrazine-2-carboxamide (0.272 g, 0.92 mmol) and Pd(dppf)Cl$_2$ (32 mg, 0.04 mmol). The resulting mixture was heated at 55° C. overnight. Silica was added, the solvent was evaporated and the crude mixture was purified by column chromatography using ethyl acetate as the eluent, followed by chloroform, then using chloroform/methanol, (98:2), to give 0.335 g (58% yield) of the base as a yellow solid: $^{13}$C NMR (DMSO-d$_6$) δ 165.4, 154.3, 163.6, 151.2, 146.8, 146.7, 145.3, 144.8, 143.6, 137.8, 134.9, 129.4, 129.4, 129.0, 123.7, 123.4, 122.1, 115.2, 113.9, 113.7, 79.4, 67.0, 6.5, 57.2, 53.9.

Hydrochloric acid in diethyl ether (0.28 mL, 1 M) was added to a solution of the base (0.324 g, 0.74 mmol) in methylene chloride/methanol, (9:1). The yellow precipitate was filtered off, washed with ethyl acetate, and then purified by preparative HPLC (column: XTerra C8 19×300 mm, eluent: a water/acetonitrile/ammonium acetate gradient). The acetonitrile in the fractions that contained the purified product were evaporated, an aqueous saturated sodium hydrogencarbonate solution was added and extracted, twice, is with methylene chloride. The organic phase was dried (MgSO$_4$) and the solvent was evaporated giving the base again. Hydrochloride acid in diethyl ether (0.56 mL, 1 M) was added to a solution of the base (0.123 g, 0.28 mmol) in methylene chloride/ methanol, (9:1). The yellow precipitate was filtered off, washed with diethyl ether and dried in vacuo to give 120 mg (90% yield) of the title compound as a yellow solid: $^1$H NM (D$_2$O) δ 9.37 (d, J=2 Hz, 1H), 8.62 (m, 1H), 8.57 (d, J=6 Hz, 1H), 8.55 (s, 1H), 8.04 (dd, J=8 and 6 Hz, 1H), 7.74 (dd, J=13 and 2 Hz, 1H), 7.64 (m, 1H), 7.15 (t, J=9 Hz, 1H), 4.49 (t, J=5 Hz, 2H), 4.14 (br s, 2H), 3.91 (br s, 2H), 3.73 (t, J=5 Hz, 2H), 3.66 (br s, 2H), 3.39 (br s, 2H); MS (ESP) m/z 440 (M$^+$+1).

The following Examples, 32-34, were synthesized as described for Example 31:

Example 32

3-Amino-6-[4-[[(1-ethyl-3-piperidinyl)amino]sulfonyl]phenyl]-N-3-pyridinyl-2-pyrazinecarboxamide Hydrochloride Starting material: 4-bromo-N-(1-ethyl-3-piperidinyl)benzenesulfonamide. The crude product was purified on silica using chloroform/methanol, (95:5), as the eluent. Yield 39% of the base.

Hydrochloride, yield: 71%: $^1$H NMR (D$_2$O) δ 9.38 (s, 1H), 8.70 (s, 1H), 8.63 (d, J=9 Hz, 1H), 8.59 (d, J=9 Hz, 1H), 8.13 (d, J=8 Hz, 2H), 8.06 (dd, J=8 and 6 Hz, 1H), 7.86 (d, J=8 Hz, 2H), 3.55 (m, 1H), 3.45 (m, 2H), 3.45 (m, 2H), 3.12 (m, 2H), 2.73 (m, 1H), 1.54 (m, 4H), 1.31 (t, J=7 Hz, 1H), 8.63 (d, J=7 Hz, 2H), 1.16 (t, J=7 Hz, 1H); $^{13}$C NMR D$_2$O) δ 165.3, 154.1, 145.5, 140.0, 139.0, 137.6, 137.0, 132.9, 128.0, 127.6, 66.4, 55.3, 52.4, 48.3, 28.4, 21.7, 14.5; MS (TSP) m/z 482 (M$^+$+1).

Example 33

3-Amino-6-[4-[[bis(2-methoxyethyl)amino]sulfonyl]phenyl]-N-3-pyridinyl-2-pyrazinecarboxamide Hydrochloride Starting material: 4-bromo-N,N-bis(2-methoxyethyl)benzenesulfonamide. The crude product was purified on silica using heptane/ethylacetate, (1:1), as eluent. Yield: 62% of the base. $^1$H NMR (CDCl$_3$) δ 9.79 (s, 1H), 8.82 (s, 1H), 8.73 (s, 1H), 8.41 (d, J=8 Hz, 1H), 8.25 (m, 1H), 8.03 (d, J=8 Hz, 2H), 7.99 (d, J=8 Hz, 2H), 7.33 (m, 1H), 3.54 (t, J=6 Hz, 4H), 3.41 (t, J=6 Hz, 4H), 3.25 (s, 6H); $^{13}$C NMR (CDCl$_3$) δ 164.4, 154.8, 146.0, 145.7, 141.8, 140.1, 139.9, 138.8, 134.2, 128.2, 127.3, 126.2, 124.6, 124.0, 71.7, 59.0, 48.9.

Hydrochloride, yield 78%: $^1$H NMR (DMSO-d$_6$) δ 9.38 (s, 1H), 9.05 (s, 1H), 8.88 (d, J=8 Hz, 1H), 8.65 (d, J=5 Hz, 1H), 8.42 (d, J=8 Hz, 2H), 8.03 (m, 1H), 7.87 (d, J=8 Hz, 2H), δ 3.41 (t, J=6 Hz, 4H), 3.30 (t, J=6 Hz, 4H), 3.18 (s, 6H); MS (ESP) m/z 487 (M$^+$+1).

Example 34

3-Amino-6-[4-[[(3-methylbutyl)amino]sulfonyl]phenyl]-N-3-pyridinyl-2-pyrazinecarboxamide Hydrochloride Starting material: 4-bromo-N-(3-methylbutyl)benzenesulfonamide. The crude product was purified on silica using heptane/ethylacetate, (2:1 to 1:2), as eluent. Yield: 62% of the base: $^1$H NMR (DMSO-d$_6$) δ 9.03 (s, 1H), 8.99 (d, J=2 Hz, 1H), 8.42 (d, J=8 Hz, 2H), 8.33 (m, 1H), 8.18 (m, 1H), 7.87 (d, J=8 Hz, 2H), 7.83 (br s, 2H), 7.61 (m, 1H), 7.39 (dd, J=8 and 5 Hz, 1H), 2.69 (q, J=7 Hz, 2H), 1.50 (sept, J=7 Hz, 1H), 1.20 (q, J=7 Hz, 2H), 0.80 (s, 3H), 0.78 (s, 3H).

Hydrochloride, yield 78%: $^1$H NMR (DMSO-d$_6$) δ 9.38 (d, J=2 Hz, 1H), 9.05 (s, 1H), 8.91 (d, J=9 Hz, 1H), 8.69 (d, J=5 Hz, 1H), 8.45 (d, J=8 Hz, 2H), 8.06 (dd, J=9 and 6 Hz, 1H), 7.84 (d, J=8 Hz, 2H), 7.62 (br s, 1H), 2.71 (br s, 2H), 1.50 (sept, J=7 Hz, 1H), 1.23 (quart, J=7 Hz, 2H), 0.80 (s, 3H), 0.78 (s, 3H); MS (ESP) m/z 442 (M$^+$+1).

Example 35

3-Amino-6-[4-[[[(1S)-2-methoxy-1-methylethyl]amino]carbonyl]phenyl]-N-3-pyridinyl-2-pyrazinecarboxamide Hydrochloride Triethylamine (0.12 mL, 0.89 mmol) was added to a mixture of 4-{5-amino-6-[(pyridin-3-ylamino)carbonyl]pyrazin-2-yl}benzoic acid (100 mg, 0.30 mmol), O-(benzotriazol-1-yl)-N,N,N',N'-tetramethyluronium tetrafluoroborate (0.105 g, 0.33 mmol) and 1-hydroxybenzotriazole (44 mg, 0.33 mmol) in methylene chloride/methanol (9:1, 10 mL) at room temperature. (S)-(+)-1-methoxy-2-propylamine was added dropwise and the resulting mixture was stirred at room temperature for 1.5 h. The mixture was evaporated onto silica and purified by chromatography on silica using toluene/acetonitrile, (2:1 to 0:1) as the eluent. The formed yellow solid was dissolved in methylene chloride. Hydrochloride acid in diethyl ether (0.4 mL, 1 M) was added and the mixture was stirred at room temperature. The precipitated product was filtrated off and dried in vacuo at 40° C. giving 39 mg (29% yield) of the product as a yellow solid. $^1$H NMR (DMSO-d$_6$) δ 9.38 (m, 1H), 9.08 (s, 1H), 8.85 (d, J=9 Hz, 1H), 8.67 (d, J=5 Hz, 1H), 8.36 (d, J=8 Hz, 2H), 8.32 (d, J=8 Hz, 2H), 8.03 (m, J=6 Hz, 1H), 7.99 (d, J=8 Hz, 2H), 7.80 (br s, 1H), 4.23 (m, 1H), 3.45 (m, 1H), 3.32 (m, 1H), 3.29 (s, 3H), 1.17 (d, J=7 Hz, 3H); $^{13}$C NMR (D$_2$O) δ 165.8, 165.5, 154.9, 146.3, 138.2, 138.1, 137.5, 135.6, 134.3, 128.0, 126.9, 125.6, 123.0, 75.3, 58.4, 44.8, 17.6; MS (ESP) m/z 407 (M$^+$+1).

Example 36

3-Amino-N-3-pyridinyl-6-[4-[[[2-(1-pyrrolidinyl)ethyl]amino]carbonyl]phenyl]-2-pyrazinecarboxamide Hydrochloride The title compound was prepared as described for Example 35 using 1-(2-aminoethyl)pyrrolidine. The crude product was purified on silica using chloroform/methanol, (95:5), as eluent. Hydrochloride, yield 23%: $^1$H NMR (D$_2$O) δ 9.33 (s, 1H), 8.67 (s, 1H), 8.55 (d, J=6 Hz, 2H), 8.0 (m, 3H), 7.82 (d, J=8 Hz, 2H), 3.83 (t, J=6 Hz, 4H), 4.53 (t, J=6 Hz, 2H), 3.23 (m, 2H), 2.23 (m, 2H), 2.09 (m, 2H); $^{13}$C NMR (D$_2$O) δ 170.3, 165.4, 154.0, 145.5, 138.8, 137.5, 136.4, 133.6, 132.7, 128.2, 127.6, 125.7, 123.8, 55.0, 54.3, 36.6, 23.0; MS (ESP) m/z 432 (M$^+$+1).

Example 37

3-Amino-N-(3-methoxyphenyl)-6-[4-[(4-methyl-1-piperazinyl)sulfonyl]phenyl]-2-pyrazinecarboxamide Hydrochloride Triethylamine (0.48 mL, 3.44 mmol) was added to a mixture of 3-amino-6-bromo-2-pyrazinecarboxylic acid (0.25 g, 1.15 mmol; described in: Ellingson, R. C.; Henry, R. L. *J. Am. Chem. Soc.* 1949, 2798-2800), O-(benzotriazol-1-yl)-N,N,N',N'-tetramethyluronium tetrafluoroborate (0.405 g, 1.26 mmol) and 1-hydroxybenzotriazole (0.17 g, 1.26 mmol) in N,N-dimethylformamide/acetonitrile, (1:1, 5 mL). After stirring for 0.5 h at room temperature, 3-methoxyaniline (0.15 mL, 1.38 mmol) was added and the resulting mixture was stirred overnight at room temperature. Water (5-10 mL) was added and the precipitate was filtered off and washed with water to give 0.25 g (68% yield) of a yellow solid: MS (ESP) m/z 323, 325 (M$^+$+1).

The solid (0.19 g, 0.59 mmol) from previous step was dissolved in tetrahydrofuran/water, (5:1, 5 mL), together with 4-[(4-methylpiperazin-1-yl)sulfonyl]phenylboronic acid (0.25 g, 0.88 mmol), sodium carbonate (0.187 g, 1.76 mmol) and Pd(dppf)Cl$_2$ (14 mg, 0.018 mmol). The resulting mixture was stirred at 70° C. overnight (N$_2$-atmosphere). The mixture was evaporated onto silica and purified by chromatography using a gradient toluene/acetonitrile, (4:1 to 1:2), as the eluent to give 82 mg (29% yield) a yellow solid which was dried in vacuo at 40° C. 48 mg of the base was dissolved in a methylene chloride/methanol mixture, (9:1), and hydrochloride acid in diethyl ether (0.13 mL, 1 M) was added. The precipitate was washed with diethyl ether and dried in vacuo to give 37 mg (63% yield) of the title compound: $^1$H NMR (DMSO-d$_6$) δ 9.05 (s, 1H), 8.54 (d, J=8 Hz, 2H), 7.86 (d, J=8 Hz, 2H), 7.51 (m, 1H), 7.44 (d, J=8 Hz, 1H), 7.30 (m, 1H), 6.75 (m, 1H), 3.83 (d, J=12 Hz, 2H), 3.78 (s, 3H), 3.44 (m, 2H), 3.16 (m, 2H), 2.73 (m, 5H); $^{13}$C NMR (DMSO-d$_6$) δ 164.3, 159.5, 154.7, 145.4, 140.6, 139.0, 136.2, 133.4, 129.4, 128.0, 126.4, 124.5, 113.3, 109.8, 106.8, 55.1, 51.5, 43.1, 41.9; MS (ESP) m/z 483 (M$^+$+1).

The following Examples, 38-41, were synthesized as described for Example 37.

Example 38

N-(3-Acetylphenyl)-3-amino-6-[4-[(4-methyl-1-piperazinyl)sulfonyl]phenyl]-2-pyrazinecarboxamide Hydrochloride Starting material: 3-acetylaniline. The title compound was purified by chromatography on silica gel using a gradient toluene/acetonitrile, (4:1 to 0:1), as the eluent, followed by formation of the hydrochloride salt, yield 2%: $^1$NMR (DMSO-d$_6$) δ 10.7 (s, 1H), 9.07 (s, 1H), 8.57 (d, J=8 Hz, 2H), 8.43 (s, 1H), 8.12 (d, J=9 Hz, 1H), 7.87 (d, J=8 Hz, 2H), 7.78 (d, J=8 Hz, 1H), 7.56 (d, J=8 Hz, 1H), 3.84 (d, J=12 Hz, 2H), 3.46 (d, J=12 Hz, 2H), 3.17 (m, 2H), 2.75 (s, 3H), 2.70 (m, 2H), 2.62 (s, 3H); $^{13}$C NMR (DMSO-d$_6$) δ 197.6, 164.6, 154.7, 145.5, 140.6, 138.2, 137.2, 136.2, 133.2, 128.9, 128.0, 126.4, 125.7, 124.2, 120.4, 51.5, 43.0, 41.8, 26.8; MS (ESP) m/z 495 (M$^+$+1).

Example 39

3-Amino-6-[4-[(4-methyl-1-piperazinyl)sulfonyl]phenyl]-N-[3-(trifluoromethyl)phenyl]-2-pyrazinecarboxamide Hydrochloride Starting material: 3-trifluoromethylaniline. Purification of the title compound by preparative HPLC (column: XTerra C8 19×300 mm, eluent: a water/acetonitrile/ammonium acetate gradient), followed by formation of the hydrochloride salt gave the title compound in 8% yield: $^1$H NMR (DMSO-d$_6$) δ 8.38 (s, 1H), 7.71 (m, 2H), 7.54 (m, 3H), 7.26 (m, 1H) 7.0 (m, 2H), 3.52 (m, 4H), 3.20 (m, 4H), 2.95 (s, 3H); MS (ESP) m/z 521.

Example 40

N-[3-(Acetylamino)phenyl]-3-amino-6-[4-[(4-methyl-1-piperazinyl)sulfonyl]phenyl]-2-pyrazinecarboxamide Starting material: 3-aminoacetanilide. The title compound was purified by chromatography on silica gel using a gradient toluene/acetonitrile, (4:1 to 0:1), as the eluent. Yield: 55% of the title compound as a yellow solid: $^1$H NMR (DMSO-d$_6$) δ 10.43, (s, 1H), 10.01 (s, 1H), 9.02 (s, 1H), 8.50 (d, J=8 Hz, 2H), 8.09 (s, 1H), 7.86 (br s, 1H), 7.81 (d, J=8 Hz, 2H), 7.42 (m, 2H), 7.30 (t, J=8 Hz, 2H), 2.96 (br s, 4H), 2.45 (br s, 4H), 2.21 (br s, 3H), 2.06 (s, 3H); $^{13}$C NMR (DMSO-d$_6$) δ 168.3, 165.3, 154.7, 145.3, 140.3, 139.5, 138.0, 136.4, 133.8, 128.7, 127.9, 126.2, 124.5, 116.2, 115.2, 112.1, 53.3, 45.7, 45.5, 25.1; MS (ESP) m/z 510 (M$^+$+1).

Example 41

3-Amino-N-[3-(aminosulfonyl)phenyl]-6-[4-[(4-methyl-1-piperazinyl)sulfonyl]phenyl]-2-pyrazinecarboxamide Starting material: 3-aminobenzenesulphonamide. Purification of the title compound by preparative HPLC (column: XTerra C8 19×300 mm, eluent: a water/acetonitrile/ammonium acetate gradient) gave 9% yield of the title compound as a yellow solid: $^1$H NMR (DMSO-d$_6$) δ 9.04 (s, 1H), 8.51 (d, J=8 Hz, 2H), 8.43 (s, 1H), 8.01 (m, 1H), 7.87 (br s, 2H), 7.81 (d, J=8 Hz, 2H), 7.61 (m, 2H), 7.40 (s, 2H), 2.94 (m, 4H), 2.37 (m, 4H), 2.14 (s, 3H); $^{13}$C NMR (DMSO-d$_6$) δ 164.7, 154.7, 145.6, 144.6, 140.2, 138.3, 136.6, 133.9, 129.2, 127.9, 126.3, 124.2, 124.1, 121.2, 118.1, 53.5, 45.7, 45.3; MS (ESP) m/z 532 (M$^+$+1).

Example 42

4-{5-Amino-6-[(pyridin-3-ylamino)carbonyl]pyrazin-2-yl}benzoic Acid

Pd(PPh$_3$)$_4$ (1.05 g, 0.91 mmol) was added to a to a solution of 3-amino-6-bromo-N-pyridin-3-ylpyrazine-2-carboxamide (2.0 g, 6.8 mmol), 4-carboxyphenylboronic acid (1.12 g, 6.7 mmol), and sodium carbonate (2.88 g, 27.2 mmol) in tetrahydrofuran/water, (1:1, 240 mL), and the resulting mixture was heated at 75° C. for 16 days. The solvent was evaporated and the residue dissolved in water. The aqueous phase was washed with ethyl acetate and then neutralized (pH 7) using HCl (10% aq.). The formed crystals were filtered off and dried in vacuo to give 1.7 g (77% yield) of the title compound: MS (ES) m/z 336 (M$^+$+1).

Example 43

4-Bromo-N-(2-ethoxyethyl)benzenesulfonamide (2-Ethoxyethyl)amine (0.178 g, 2.0 mmol) was added to a stirred solution of 4-bromobenzenesulfonyl chloride (0.256 g, 1.0 mmol) in tetrahydrofuran (10 mL) at 0 C, followed by addition of N-ethyl-N,N-diisopropylamine (0.260 g, 2.0 mmol). The resulting mixture was stirred at 0° C. for 10 min, and was then allowed to return to room temperature. A saturated solution of NaHCO$_3$ (aq) was added and the phases were separated, and the aqueous phase was extracted with ethyl acetate. The combined organic phases were dried over Na$_2$SO$_4$, and the solvent was evaporated to give the crude product. Purification by column chromatography using ethyl acetate/heptane (1:10 to 1:1) as the eluent gave 0.278 g (90% yield) of the title compound: MS (ES) m/z 294 and 296 (M$^+$+1).

Example 44

3-Amino-6-(4-{[(2-ethoxyethyl)amino]sulfonyl}phenyl)-N-pyridin-3-ylpyrazine-2-carboxamide Hydrochloride The title compound was prepared as described Example 17 using 4-bromo-N-(2-ethoxyethyl)benzenesulfonamide. Yield: 10%: $^1$H NMR (D$_2$O, 400 MHz) δ 9.29 (d, J=3 Hz, 1H), 8.56 (s, 1H), 8.54 (m, 1H), 8.52 (m, 1H), 8.01 (dd, J=9, 6 Hz, 1H), 7.98 (d, J=9 Hz, 2H), 7.71 (d, J=9 Hz, 2H), 3.45 (t, J=5 Hz, 2H), 3.41 (q, J=7 Hz, 2H), 3.07 (t, J=5 Hz, 2H), 1.05 (t, J=7 Hz, 3H); MS (ES) m/z 443 (M$^+$+1).

Pharmaceutical Compositions

According to one aspect of the present invention there is provided a pharmaceutical composition comprising a compound of formula I, as a free base or a pharmaceutically acceptable salt, solvate or solvate of salt thereof, for use in the prevention and/or treatment of conditions associated with glycogen synthase kinase-3.

The composition may be in a form suitable for oral administration, for example as a tablet, for parenteral injection as a sterile solution or suspension. In general the above compositions may be prepared in a conventional manner using pharmaceutical carriers or diluents. Suitable daily doses of the compounds of formula I in the treatment of a mammal, including man, are approximately 0.01 to 250 mg/kg bodyweight at peroral administration and about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

A compound of formula I, or a pharmaceutically acceptable salt, solvate or solvate of salt thereof, can be used on its own but will usually be administered in the form of a pharmaceutical composition in which the formula I compound/salt/solvate (active ingredient) is in association with a pharmaceutically acceptable diluent or carrier. Dependent on the mode of administration, the pharmaceutical composition may comprise from 0.05 to 99% w (per cent by weight), for example from 0.10 to 50% w, of active ingredient, all percentages by weight being based on total composition.

A diluent or carrier includes water, aqueous poly(ethylene glycol), magnesium carbonate, magnesium stearate, talc, a sugar (such as lactose), pectin, dextrin, starch, tragacanth, microcrystalline cellulose, methyl cellulose, sodium carboxymethyl cellulose or cocoa butter.

A composition of the invention can be in tablet or injectable form. The tablet may additionally comprise a disintegrant and/or may be coated (for example with an enteric coating or coated with a coating agent such as hydroxypropyl methylcellulose).

The invention further provides a process for the preparation of a pharmaceutical composition of the invention which comprises mixing a compound of formula I, or a pharmaceutically acceptable salt, solvate or solvate of salt thereof, a hereinbefore defined, with a pharmaceutically acceptable diluent or carrier.

An example of a pharmaceutical composition of the invention is an injectable solution containing a compound of the invention, or a pharmaceutically acceptable salt, solvate or solvate of salt thereof, as hereinbefore defined, and sterile water, and, if necessary, either sodium hydroxide or hydrochloric acid to bring the pH of the final composition to about pH 5, and optionally a surfactant to aid dissolution.

Liquid solution comprising a compound of formula I, as a free base or a pharmaceutically acceptable salt, solvate or solvate of a salt thereof, dissolved in water.

| Solution | mg/mL |
| --- | --- |
| Compound X | 5.0% w/v |
| Pure water | To 100% |

Medical Use

Surprisingly, it has been found that the compounds defined in the present invention, as a free base or a pharmaceutically acceptable salt, solvate or solvate of a salt thereof, are well suited for inhibiting glycogen synthase kinase-3 (GSK3). Accordingly, the compounds of the present invention are expected to be useful in the prevention and/or treatment of conditions associated with glycogen synthase kinase-3 activity, i.e. the compounds may be used to produce an inhibitory effect of GSK3 in mammals, including man, in need of such prevention and/or treatment.

GSK3 is highly expressed in the central and peripheral nervous system and in other tissues. Thus, it is expected that compounds of the invention are well suited for the prevention and/or treatment of conditions associated with glycogen synthase kinase-3 in the central and peripheral nervous system. In particular, the compounds of the invention are expected to be suitable for prevention and/or treatment of conditions associated with especially, dementia, Alzheimer's Disease, Parkinson's Disease, Frontotemporal dementia Parkinson's Type, Parkinson dementia complex of Guam, HIV dementia, diseases with associated neurofibrillar tangle pathologies and dementia pugilistica.

Other conditions are selected from the group consisting of amyotrophic lateral sclerosis, corticobasal degeneration, Down syndrome, Huntington's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, schizophrenia, cognitive disorders, hair loss, contraceptive medication, Type I and Type II diabetes, diabetic neuropathy and diabetes related disorders.

Further conditions are selected from the group consisting predemented states, Mild Cognitive Impairment, Age-Associated Memory Impairment, Age-Related Cognitive Decline, Cognitive Impairment No Dementia, mild cognitive decline, mild neurocognitive decline, Late-Life Forgetfulness, memory impairment and cognitive impairment, vascular dementia, dementia with Lewy bodies and androgenetic alopecia.

One embodiment of the invention relates to the prevention and/or treatment of dementia and Alzheimer's Disease.

The dose required for the therapeutic or preventive treatment of a particular disease will necessarily be varied depending on the host treated, the route of administration is and the severity of the illness being treated.

The present invention relates also to the use of a compound of formula I as defined hereinbefore, in the manufacture of a medicament for the prevention and/or treatment of conditions associated with glycogen synthase kinase-3.

In the context of the present specification, the term "therapy" also includes "prevention" unless there are specific indications to the contrary. The terms "therapeutic" and "therapeutically" should be construed accordingly.

The invention also provides for a method of treatment and/or prevention of conditions associated with glycogen synthase kinase-3 comprising administering to a mammal, including man in need of such treatment and/or prevention a therapeutically effective amount of a compound of formula I, as hereinbefore defined.

Non-Medical Use

In addition to their use in therapeutic medicine, the compounds of formula I as a free base or a pharmaceutically acceptable salt, solvate or solvate of a salt thereof, are also useful as pharmacological tools in the development and standardisation of in vitro and in vivo test systems for the evaluation of the effects of inhibitors of GSK3 related activity in laboratory animals such as cats, dogs, rabbits, monkeys, rats and mice, as part of the search for new therapeutics agents.

Pharmacology

Determination of ATP Competition in Scintillation Proximity GSK3β Assay.

GSK3β Scintillation Proximity Assay.

The competition experiments were carried out in duplicate with 10 different concentrations of the inhibitors in clear-bottom microtiter plates (Wallac, Finland). A biotinylated peptide substrate, Biotin-Ala-Ala-Glu-Glu-Leu-Asp-Ser-Arg-Ala-Gly-Ser(PO$_3$H$_2$)-Pro-Gln-Leu (AstraZeneca, Lund), was added at a final concentration of 1 μM in an assay buffer containing 1 mU recombinant human GSK3β (Dundee University, UK), 12 mM morpholinepropanesulfonic acid (MOPS), pH 7.0, 0.3 mM EDTA, 0.01% β-mercaptoethanol, 0.004% Brij 35 (a natural detergent), 0.5% glycerol and 0.5 μg BSA/25 μl. The reaction was initiated by the addition of 0.04 μCi [γ-$^{33}$P]ATP (Amersham, UK) and unlabelled ATP at a final concentration of 1 μM and assay volume of 25 μl. After incubation for 20 minutes at room temperature, each reaction was terminated by the addition of 25 μl stop solution containing 5 mM EDTA, 50 μM ATP, 0.1% Triton X-100 and 0.25 mg streptavidin coated Scintillation Proximity Assay (SPA) beads (Amersham, UK). After 6 hours the radioactivity was determined in a liquid scintillation counter (1450 MicroBeta Trilux, Wallac). The inhibition curves were analysed by non-linear regression using GraphPad Prism, USA. The $K_m$ value of ATP for GSK3β, used to calculate the inhibition constants ($K_i$) of the various compounds, was 20 μM.

The following abbreviations have been used:

| | |
|---|---|
| MOPS | Morpholinepropanesulfonic acid |
| EDTA | Ethylenediaminetetraacetic acid |
| BSA | Bovin Serum Albumin |
| ATP | Adenosine Triphosphate |
| SPA | Scintillation Proximity Assay |
| GSK3 | Glycogen synthase kinase 3 |

Results

Typical $K_i$ values for the compounds of the present invention are in the range of about 0.001 to about 10,000 nM. Other values for $K_i$ are in the range of about 0.001 to about 1000 nM. Further values for $K_i$ are in the range of about 0.001 nM to about 300 nM.

The invention claimed is:

1. A compound of the generic formula I:

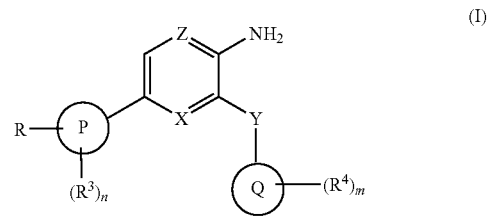

wherein:
Z is N;
Y is CONR$^5$;
X is N;
P is phenyl;
Q is phenyl;
R is selected from C$_{0-6}$alkyl(SO$_2$)NR$^1$R$^2$, C$_{0-6}$alkylCONR$^1$R$^2$ and OC$_{1-6}$alkylNR$^1$R$^2$;
R$^1$ and R$^2$ are independently selected from hydrogen, C$_{1-6}$alkyl, C$_{1-6}$alkylNR$^6$R$^7$, C$_{1-6}$alkylOR$^6$ and 3-piperidinyl wherein said C$_{1-6}$alkyl or 3-piperidinyl may have a C$_{1-6}$alkyl substituent thereon; or
R$^1$ and R$^2$ may together form a 1-pyrrolidinyl, 1-piperazinyl or 4-morpholinyl moiety wherein said 1-pyrrolidinyl, 1-piperazinyl or 4-morpholinyl moiety may have a C$_{1-6}$alkyl substituent thereon;
R$^3$ and R$^4$ are independently selected from halo, nitro, trifluoromethyl, C$_{0-6}$alkylCN, C$_{0-6}$alkylOR$^6$, C$_{0-6}$alkylCONR$^6$R$^7$, C$_{0-6}$alkylNR$^6$(CO)R$^7$, C$_{0-6}$alkylCOR$^6$, C$_{0-6}$alkyl(SO$_2$)NR$^6$R$^7$;
m is 0 or 1;
n is 0 or 1;
R$^5$ is hydrogen;
R$^6$ and R$^7$ are independently selected from hydrogen and C$_{1-6}$alkyl; or
R$^6$ and R$^7$ may together form a 1-pyrrolidinyl moiety wherein said 1-pyrrolidinyl may have a C$_{1-6}$alkyl substituent thereon;
as a free base or a pharmaceutically acceptable salt thereof.

2. A compound according to claim 1 which is:
3-Amino-N-(3-nitrophenyl)-6-[4-(pyrrolidin-1-ylsulfonyl)phenyl]pyrazine-2-carboxamide;
N-[3-(Acetylamino)phenyl]-3-amino-6-[4-[(4-methyl-1-piperazinyl)sulfonyl]phenyl]-2-pyrazinecarboxamide;
3-Amino-N-[3-(aminosulfonyl)phenyl]-6-[4-[(4-methyl-1-piperazinyl)sulfonyl]phenyl]-2-pyrazinecarboxamide;
3-Amino-N-(2-methoxyphenyl)-6-{4-[(4-methylpiperazin-1-yl)sulfonyl]phenyl}pyrazine-2-carboxamide hydrochloride;
3-Amino-N-(4-methoxyphenyl)-6-{4-[(4-methylpiperazin-1-yl)sulfonyl]phenyl}pyrazine-2-carboxamide hydrochloride;
3-Amino-N-[2-(aminocarbonyl)phenyl]-6-{4-[(4-methylpiperazin-1-yl)sulfonyl]phenyl}pyrazine-2-carboxamide hydrochloride;
3-Amino-N-[3-(aminocarbonyl)phenyl]-6-{4-[(4-methylpiperazin-1-yl)sulfonyl]phenyl}pyrazine-2-carboxamide hydrochloride;
3-Amino-N-(3-cyanophenyl)-6-{4-[(4-methylpiperazin-1-yl)sulfonyl]phenyl}pyrazine-2-carboxamide hydrochloride;

3-Amino-N-(2-bromophenyl)-6-{4-[(4-methylpiperazin-1-yl)sulfonyl]phenyl}pyrazine-2-carboxamide hydrochloride;

3-Amino-N-(3-bromophenyl)-6-{4-[(4-methylpiperazin-1-yl)sulfonyl]phenyl}pyrazine-2-carboxamide hydrochloride;

3-Amino-N-(3-methoxyphenyl)-6-[4-[(4-methyl-1-piperazinyl)sulfonyl]phenyl]-2-pyrazinecarboxamide hydrochloride;

N-(3-Acetylphenyl)-3-amino-6-[4-[(4-methyl-1-piperazinyl)sulfonyl]phenyl]-2-pyrazinecarboxamide hydrochloride, or 3-Amino-6-[4-[(4-methyl-1-piperazinyl)sulfonyl]phenyl]-N-[3-(trifluoromethyl)phenyl]-2-pyrazinecarboxamide hydrochloride;

or a free base of any said hydrochloride or a pharmaceutically acceptable salt thereof.

3. A pharmaceutical formulation comprising as active ingredient a therapeutically effective amount of a compound according to claim 2 or 1 in association with a pharmaceutically acceptable carrier or diluent.

* * * * *

UNITED STATES PATENT AND TRADEMARK OFFICE
CERTIFICATE OF CORRECTION

PATENT NO.       : 7,595,319 B2
APPLICATION NO.  : 10/539546
DATED            : September 29, 2009
INVENTOR(S)      : Berg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 949 days.

Signed and Sealed this

Twenty-eighth Day of September, 2010

David J. Kappos
*Director of the United States Patent and Trademark Office*